(12) United States Patent
Upchurch, Jr. et al.

(10) Patent No.: US 9,597,166 B2
(45) Date of Patent: *Mar. 21, 2017

(54) ORTHODONTIC APPLIANCE WITH ENCODED INFORMATION

(71) Applicant: RMO, Inc., Denver, CO (US)

(72) Inventors: Daphne Upchurch, Jr., Lakewood, CO (US); Michael Dean Stevens, Littleton, CO (US); Paul Ritter Smith, Denver, CO (US); Ray Winston Freeman, Pine, CO (US); George Kantor, Lakewood, CO (US)

(73) Assignee: RMO, Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/654,021

(22) Filed: Oct. 17, 2012

(65) Prior Publication Data
US 2013/0280668 A1    Oct. 24, 2013

Related U.S. Application Data

(63) Continuation of application No. 13/117,070, filed on May 26, 2011, now abandoned, which is a
(Continued)

(51) Int. Cl.
*A61C 7/28*    (2006.01)
*A61C 7/14*    (2006.01)
(Continued)

(52) U.S. Cl.
CPC .............. *A61C 7/285* (2013.01); *A61C 7/143* (2013.01); *A61C 7/16* (2013.01); *A61C 7/28* (2013.01); *A61C 7/30* (2013.01)

(58) Field of Classification Search
CPC ........... A61C 7/12; A61C 7/285; A61C 7/143; A61C 7/16; A61C 7/28; A61C 7/30
(Continued)

(56) References Cited

U.S. PATENT DOCUMENTS

| 626,476 | A | 6/1899 | Angle |
|---|---|---|---|
| 1,890,487 | A | 12/1932 | Angle |

(Continued)

FOREIGN PATENT DOCUMENTS

| DE | 8903611 | 8/1990 |
|---|---|---|
| DE | 69228472 | 10/1999 |

(Continued)

OTHER PUBLICATIONS

U.S. Appl. No. 13/766,997, filed Feb. 14, 2013, Dupray et al.
(Continued)

*Primary Examiner* — Cris L Rodriguez
*Assistant Examiner* — Hao D Mai
(74) *Attorney, Agent, or Firm* — Sheridan Ross P.C.

(57) ABSTRACT

An improved edgewise orthodontic bracket is disclosed. In one embodiment, a bracket has a single pair of opposing T-shaped tie wings which define an archwire slot therebetween. Notches are provided on each of the mesial and distal sides of the center leg of each T-shaped tie wing for selectively receiving a ligating device. The notches are defined in the gingival/occlusal edges of the tie wings and comprise sloped portions that extend labially towards the archwire slot. Convex sidewall portions and convex floor portions are provided in the archwire slot adjacent to the notches. The body of the bracket is interconnected to a base that may includes a continuous series of characters that serve as texturing to facilitate bonding of the bracket with a tooth. A discontinuous perimeter rail may be used at the edge of the base.

21 Claims, 20 Drawing Sheets

Related U.S. Application Data continuation-in-part of application No. 11/782,569, filed on Jul. 24, 2007, now Pat. No. 7,959,437, which is a continuation-in-part of application No. 10/848,929, filed on May 18, 2004, now Pat. No. 7,247,018, which is a continuation-in-part of application No. 10/284,016, filed on Oct. 29, 2002, now Pat. No. 6,846,178.

(51) Int. Cl.
  *A61C 7/16* (2006.01)
  *A61C 7/30* (2006.01)

(58) Field of Classification Search
  USPC ..................................................... 433/8–16
  See application file for complete search history.

(56) References Cited

U.S. PATENT DOCUMENTS

| | | | |
|---|---|---|---|
| 2,011,575 | A | 8/1935 | Ford |
| 2,104,192 | A | 1/1938 | Ford |
| 2,196,515 | A | 4/1940 | Atkinson |
| 3,028,671 | A | 4/1962 | Berger |
| 3,055,110 | A | 9/1962 | Kesling |
| 3,158,934 | A | 12/1964 | Waldman |
| 3,193,930 | A | 7/1965 | Bien |
| 3,391,461 | A | 7/1968 | Johnson |
| 3,435,527 | A | 4/1969 | Kesling |
| 3,494,034 | A | 2/1970 | Kesling |
| 3,504,438 | A | 4/1970 | Wittman et al. |
| 3,526,961 | A | 9/1970 | Kesling |
| 3,765,091 | A | 10/1973 | Northcutt |
| 3,798,773 | A | 3/1974 | Northcutt |
| 3,838,514 | A | 10/1974 | Polak |
| 3,854,207 | A | 12/1974 | Wildman |
| 3,874,080 | A | 4/1975 | Wallshein |
| 3,916,526 | A | 11/1975 | Schudy |
| 3,964,156 | A | 6/1976 | Williams et al. |
| 3,975,824 | A | 8/1976 | Lee |
| 3,985,282 | A | 10/1976 | Miller et al. |
| 3,987,547 | A | 10/1976 | Moss |
| 4,015,334 | A | 4/1977 | Moss |
| 4,028,809 | A | 6/1977 | Wallshein |
| 4,083,113 | A | 4/1978 | Miller et al. |
| 4,103,423 | A | 8/1978 | Kessel |
| 4,134,208 | A | 1/1979 | Pearlman |
| 4,171,568 | A | 10/1979 | Forster |
| 4,172,999 | A | 10/1979 | Leidich |
| 4,183,141 | A | 1/1980 | Dellinger et al. |
| 4,192,070 | A | 3/1980 | Lemchen et al. |
| 4,193,195 | A | 3/1980 | Merkel et al. |
| 4,197,642 | A | 4/1980 | Wallshein |
| 4,212,638 | A | 7/1980 | Korn |
| 4,219,617 | A | 8/1980 | Wallshein |
| D256,950 | S | 9/1980 | Sable |
| 4,242,085 | A | 12/1980 | Wallshein |
| 4,248,587 | A | 2/1981 | Kurz |
| 4,260,375 | A | 4/1981 | Wallshein |
| 4,284,405 | A | 8/1981 | Dellinger |
| 4,299,569 | A | 11/1981 | Frantz |
| 4,302,532 | A | 11/1981 | Wallshein |
| 4,322,206 | A | 3/1982 | Reynolds |
| 4,350,487 | A | 9/1982 | Kesling et al. |
| 4,354,834 | A | 10/1982 | Wilson |
| 4,386,908 | A | 6/1983 | Kurz |
| 4,415,330 | A | 11/1983 | Daisley et al. |
| 4,419,078 | A | 12/1983 | Pletcher |
| 4,430,061 | A | 2/1984 | Webb et al. |
| 4,455,137 | A | 6/1984 | Diamond |
| 4,462,800 | A | 7/1984 | Jones |
| 4,478,577 | A | 10/1984 | Warren, Jr. |
| 4,498,867 | A | 2/1985 | Kesling |
| 4,511,331 | A | 4/1985 | Scebold et al. |
| 4,527,975 | A | 7/1985 | Ghafari et al. |
| 4,529,382 | A | 7/1985 | Creekmore |
| 4,531,911 | A | 7/1985 | Creekmore |
| 4,531,991 | A | 7/1985 | Ziemek et al. |
| 4,545,760 | A | 10/1985 | Forster |
| 4,551,095 | A | 11/1985 | Mason |
| 4,575,337 | A | 3/1986 | Fujita |
| 4,626,209 | A | 12/1986 | Tsai et al. |
| 4,639,218 | A * | 1/1987 | Jones et al. ...................... 433/8 |
| 4,659,309 | A | 4/1987 | Merkel |
| 4,661,059 | A | 4/1987 | Kanno |
| D290,040 | S | 5/1987 | Kelly |
| 4,669,979 | A | 6/1987 | Snead |
| 4,669,981 | A | 6/1987 | Kurz |
| D291,919 | S | 9/1987 | Reynolds |
| 4,700,697 | A | 10/1987 | Mundell et al. |
| 4,712,999 | A | 12/1987 | Rosenberg |
| 4,752,221 | A | 6/1988 | Hanson et al. |
| 4,773,853 | A | 9/1988 | Kussick |
| 4,781,334 | A | 11/1988 | Derichs |
| 4,781,582 | A | 11/1988 | Kesling |
| 4,793,804 | A | 12/1988 | Schudy |
| 4,795,342 | A | 1/1989 | Jones |
| 4,799,882 | A | 1/1989 | Kesling |
| 4,819,316 | A | 4/1989 | Rossini et al. |
| 4,820,151 | A | 4/1989 | Pospisil |
| 4,838,786 | A | 6/1989 | Reher et al. |
| 4,854,866 | A | 8/1989 | Wilson |
| 4,859,179 | A | 8/1989 | Kesling |
| 4,900,251 | A | 2/1990 | Andreasen |
| 4,917,602 | A | 4/1990 | Broussard |
| 4,927,360 | A | 5/1990 | Pospisil |
| 4,927,362 | A | 5/1990 | Snead |
| 4,954,080 | A | 9/1990 | Kelly et al. |
| 4,963,092 | A | 10/1990 | Snead |
| 4,975,052 | A | 12/1990 | Spencer et al. |
| 4,997,182 | A | 3/1991 | Kussick |
| 5,022,854 | A | 6/1991 | Broughton et al. |
| 5,030,089 | A | 7/1991 | Kawaguchi |
| 5,035,614 | A | 7/1991 | Greenfield |
| 5,044,945 | A * | 9/1991 | Peterson ........................... 433/8 |
| 5,057,012 | A | 10/1991 | Kesling |
| 5,059,119 | A | 10/1991 | Snead |
| 5,062,794 | A | 11/1991 | Miura |
| 5,066,225 | A | 11/1991 | Forbes Jones et al. |
| D322,482 | S | 12/1991 | Ianieri et al. |
| 5,095,602 | A | 3/1992 | Reher et al. |
| 5,120,218 | A | 6/1992 | Hanson |
| 5,125,831 | A | 6/1992 | Pospisil |
| 5,125,832 | A | 6/1992 | Kesling |
| 5,127,828 | A | 7/1992 | Suyama |
| 5,133,740 | A | 7/1992 | Kussick |
| 5,151,028 | A | 9/1992 | Snead |
| 5,154,607 | A | 10/1992 | Hanson |
| 5,158,452 | A | 10/1992 | Franseen et al. |
| 5,160,261 | A | 11/1992 | Peterson |
| 5,161,969 | A | 11/1992 | Pospisil et al. |
| D331,975 | S | 12/1992 | Pospisil |
| 5,183,388 | A | 2/1993 | Kumar |
| 5,203,804 | A | 4/1993 | Nikutowski et al. |
| 5,224,858 | A | 7/1993 | Hanson |
| 5,226,814 | A | 7/1993 | Allen |
| 5,230,620 | A | 7/1993 | Watanabe |
| 5,238,402 | A | 8/1993 | Rohlcke et al. |
| 5,242,299 | A | 9/1993 | Yoshida |
| D340,523 | S | 10/1993 | Barngrover |
| 5,252,066 | A | 10/1993 | Fairhurst |
| 5,254,002 | A | 10/1993 | Reher et al. |
| 5,267,855 | A | 12/1993 | Tuneberg |
| 5,269,680 | A | 12/1993 | Kawaguchi |
| 5,277,581 | A | 1/1994 | Peterson |
| 5,288,229 | A | 2/1994 | Huff et al. |
| 5,292,248 | A | 3/1994 | Schultz |
| 5,299,934 | A | 4/1994 | Suyama |
| 5,302,117 | A | 4/1994 | Kraut et al. |
| 5,302,121 | A | 4/1994 | Gagin |
| 5,320,525 | A | 6/1994 | Forster |
| 5,320,526 | A | 6/1994 | Tuneberg |
| 5,322,435 | A | 6/1994 | Pletcher |
| 5,322,613 | A | 6/1994 | Ohira |

(56) References Cited

U.S. PATENT DOCUMENTS

| | | |
|---|---|---|
| 5,356,288 A | 10/1994 | Cohen |
| 5,358,402 A | 10/1994 | Reed et al. |
| 5,362,232 A * | 11/1994 | Franseen et al. .............. 433/9 |
| 5,362,233 A | 11/1994 | Thompson |
| 5,380,196 A | 1/1995 | Kelly et al. |
| 5,383,784 A | 1/1995 | Sernetz |
| 5,395,238 A | 3/1995 | Andreiko et al. |
| D358,649 S | 5/1995 | Moschik |
| D358,650 S | 5/1995 | Moschik |
| D359,776 S | 6/1995 | Hilgers |
| 5,439,379 A | 8/1995 | Hansen |
| 5,441,408 A | 8/1995 | Moschik |
| 5,441,409 A | 8/1995 | Tuneberg |
| 5,443,384 A | 8/1995 | Franseen et al. |
| 5,454,716 A | 10/1995 | Banerjee et al. |
| 5,464,349 A | 11/1995 | Andreiko et al. |
| 5,470,228 A * | 11/1995 | Franseen et al. .............. 433/8 |
| 5,474,444 A | 12/1995 | Wildman |
| 5,474,445 A | 12/1995 | Voudouris |
| 5,505,616 A | 4/1996 | Harwell |
| 5,522,725 A | 6/1996 | Jordan et al. |
| 5,545,037 A | 8/1996 | Takeshi |
| 5,556,277 A | 9/1996 | Yawata et al. |
| 5,562,445 A | 10/1996 | DeVincenzo et al. |
| 5,588,833 A | 12/1996 | Risse |
| 5,595,484 A | 1/1997 | Orikasa et al. |
| 5,597,302 A | 1/1997 | Pospisil et al. |
| 5,607,301 A | 3/1997 | Roman |
| 5,616,026 A | 4/1997 | Cash |
| 5,618,175 A | 4/1997 | Reher et al. |
| 5,620,321 A | 4/1997 | Thornburg et al. |
| 5,622,494 A | 4/1997 | Andreiko et al. |
| 5,653,588 A | 8/1997 | Moschik |
| 5,685,711 A | 11/1997 | Hanson |
| 5,692,898 A | 12/1997 | Orikasa et al. |
| 5,707,231 A | 1/1998 | Watt et al. |
| 5,720,611 A | 2/1998 | Teng |
| 5,727,941 A | 3/1998 | Kesling |
| 5,729,768 A | 3/1998 | Fields et al. |
| 5,738,514 A | 4/1998 | DeVincenzo et al. |
| 5,746,592 A | 5/1998 | Nezu et al. |
| 5,746,594 A | 5/1998 | Jordan et al. |
| RE35,863 E | 7/1998 | Sachdeva et al. |
| 5,779,470 A | 7/1998 | Kussick |
| 5,791,897 A | 8/1998 | Wildman |
| 5,810,583 A | 9/1998 | Doyle |
| 5,820,371 A | 10/1998 | Forster |
| 5,829,972 A | 11/1998 | Farzin-Nia |
| 5,829,975 A | 11/1998 | Gold |
| 5,857,849 A | 1/1999 | Kurz |
| 5,871,350 A | 2/1999 | Clark et al. |
| 5,879,157 A | 3/1999 | Scheu |
| 5,885,073 A | 3/1999 | Kussick |
| 5,885,074 A | 3/1999 | Hanson |
| 5,890,891 A | 4/1999 | Doyle |
| 5,908,293 A | 6/1999 | Voudouris |
| 5,915,550 A | 6/1999 | Gartz |
| 6,036,489 A | 3/2000 | Brosius |
| 6,053,458 A | 4/2000 | Meyer |
| 6,053,729 A | 4/2000 | Brehm et al. |
| 6,053,759 A | 4/2000 | Kunert et al. |
| 6,071,119 A | 6/2000 | Christoff et al. |
| 6,086,364 A | 7/2000 | Brunson |
| 6,109,916 A | 8/2000 | Wilcko et al. |
| 6,123,544 A | 9/2000 | Cleary |
| 6,126,441 A | 10/2000 | Tenti |
| 6,142,775 A | 11/2000 | Hansen et al. |
| 6,162,051 A | 12/2000 | Brehm et al. |
| 6,190,165 B1 | 2/2001 | Andreiko et al. |
| 6,193,508 B1 | 2/2001 | Georgakis |
| 6,206,690 B1 | 3/2001 | Vargas |
| 6,217,322 B1 | 4/2001 | Kesling |
| 6,220,857 B1 | 4/2001 | Abels |
| 6,227,849 B1 | 5/2001 | Brehm et al. |
| 6,234,792 B1 | 5/2001 | DeVincenzo |
| 6,264,469 B1 | 7/2001 | Moschik |
| 6,276,930 B1 | 8/2001 | Pozzi |
| 6,280,185 B1 | 8/2001 | Palmer et al. |
| 6,302,688 B1 | 10/2001 | Jordan et al. |
| 6,347,939 B2 | 2/2002 | Abels |
| 6,354,834 B2 | 3/2002 | Kanomi |
| 6,358,043 B1 | 3/2002 | Mottate et al. |
| 6,358,046 B1 | 3/2002 | Brehm et al. |
| 6,361,314 B1 | 3/2002 | Garton, Jr. |
| 6,361,317 B1 * | 3/2002 | Rahman .............. 433/141 |
| 6,368,105 B1 | 4/2002 | Voudouris et al. |
| 6,371,760 B1 | 4/2002 | Zavilenski et al. |
| 6,394,798 B1 | 5/2002 | Huff et al. |
| 6,428,314 B1 | 8/2002 | Jones, Jr. et al. |
| 6,461,157 B1 | 10/2002 | Kussick |
| 6,478,579 B1 * | 11/2002 | Brusse .............. 433/8 |
| 6,491,519 B1 | 12/2002 | Clark et al. |
| 6,506,049 B2 | 1/2003 | Hanson |
| 6,582,226 B2 | 6/2003 | Jordan et al. |
| 6,592,366 B2 | 7/2003 | Triaca et al. |
| 6,607,383 B2 | 8/2003 | Abels et al. |
| 6,616,445 B2 | 9/2003 | Abels et al. |
| 6,655,957 B2 | 12/2003 | Abels et al. |
| 6,655,958 B2 | 12/2003 | Abels et al. |
| 6,656,767 B1 | 12/2003 | King et al. |
| 6,659,766 B2 | 12/2003 | Abels et al. |
| 6,659,767 B2 | 12/2003 | Abels et al. |
| 6,663,385 B2 | 12/2003 | Tepper |
| 6,668,834 B1 | 12/2003 | Zikria |
| 6,695,612 B2 | 2/2004 | Abels et al. |
| 6,705,862 B2 | 3/2004 | Schultz |
| 6,709,268 B2 | 3/2004 | Pospisil et al. |
| 6,733,286 B2 | 5/2004 | Abels et al. |
| 6,769,910 B1 | 8/2004 | Pantino |
| 6,776,613 B2 | 8/2004 | Orikasa |
| 6,776,614 B2 | 8/2004 | Wiechmann et al. |
| 6,846,178 B2 | 1/2005 | Freeman, Jr. et al. |
| 6,863,528 B2 | 3/2005 | Lin |
| 6,877,982 B2 | 4/2005 | Williams |
| 6,893,257 B2 | 5/2005 | Kelly |
| 6,903,262 B2 | 6/2005 | Blersch |
| 6,910,884 B2 | 6/2005 | Kelly et al. |
| 6,913,459 B2 | 7/2005 | Fukutomi |
| 7,001,179 B2 | 2/2006 | Devincenzo |
| 7,025,591 B1 | 4/2006 | Kesling |
| 7,033,170 B2 | 4/2006 | Cordato |
| 7,033,171 B2 | 4/2006 | Wilkerson |
| 7,055,908 B1 | 6/2006 | Williams |
| 7,074,037 B2 | 7/2006 | Macchi |
| 7,094,052 B2 * | 8/2006 | Abels et al. .............. 433/8 |
| 7,140,875 B2 | 11/2006 | Lai et al. |
| 7,151,541 B2 | 12/2006 | Seder |
| 7,153,130 B2 | 12/2006 | Christoff |
| 7,210,927 B2 | 5/2007 | Abels et al. |
| 7,234,935 B2 | 6/2007 | Abels et al. |
| 7,247,018 B2 | 7/2007 | Freeman et al. |
| 7,258,545 B2 | 8/2007 | Hotta |
| 7,267,545 B2 | 9/2007 | Oda |
| 7,306,458 B1 | 12/2007 | Lu et al. |
| 7,416,408 B2 | 8/2008 | Farzin-Nia et al. |
| 7,621,743 B2 | 11/2009 | Bathen et al. |
| 7,695,277 B1 | 4/2010 | Stevens |
| 7,704,072 B2 | 4/2010 | Damon |
| 7,780,443 B2 | 8/2010 | Hagelganz |
| 7,811,087 B2 | 10/2010 | Wiechmann et al. |
| 7,850,451 B2 | 12/2010 | Wiechmann et al. |
| 7,909,603 B2 | 3/2011 | Oda |
| 7,959,437 B2 | 6/2011 | Zakhem |
| 7,963,768 B2 | 6/2011 | Hilliard |
| 8,251,697 B2 | 8/2012 | Smith et al. |
| 2001/0036615 A1 | 11/2001 | Binder |
| 2002/0025502 A1 | 2/2002 | Williams |
| 2002/0110778 A1 | 8/2002 | Abels et al. |
| 2002/0187452 A1 | 12/2002 | Abels et al. |
| 2003/0049582 A1 | 3/2003 | Abels et al. |
| 2003/0064344 A1 | 4/2003 | Vazquez |
| 2003/0088261 A1 | 5/2003 | Schraga |
| 2003/0096209 A1 | 5/2003 | Sugiyama et al. |
| 2003/0143509 A1 | 7/2003 | Kopelman et al. |

(56) References Cited

U.S. PATENT DOCUMENTS

| | | |
|---|---|---|
| 2004/0244149 A1 | 12/2004 | Anscher |
| 2004/0259048 A1 | 12/2004 | Balabanovsky |
| 2005/0069833 A1 | 3/2005 | Chikami |
| 2005/0244777 A1 | 11/2005 | Schultz |
| 2006/0014116 A1 | 1/2006 | Maijer et al. |
| 2006/0046224 A1 | 3/2006 | Sondhi et al. |
| 2006/0063123 A1 | 3/2006 | Cleary et al. |
| 2006/0099544 A1 | 5/2006 | Lai et al. |
| 2006/0099545 A1 | 5/2006 | Lai et al. |
| 2006/0199137 A1 | 9/2006 | Abels et al. |
| 2006/0228662 A1 | 10/2006 | Lokar et al. |
| 2006/0228664 A1 | 10/2006 | Castner et al. |
| 2006/0246392 A1 | 11/2006 | Vigolo |
| 2006/0252002 A1 | 11/2006 | Hanson |
| 2006/0257810 A1 | 11/2006 | Maijer et al. |
| 2006/0263737 A1 | 11/2006 | Oda |
| 2006/0269889 A1 | 11/2006 | Voudouris |
| 2007/0054231 A1 | 3/2007 | Manemann et al. |
| 2007/0092849 A1 | 4/2007 | Cosse |
| 2007/0166658 A1 | 7/2007 | Voudouris |
| 2007/0207436 A1 | 9/2007 | Tan et al. |
| 2007/0224569 A1 | 9/2007 | Oda |
| 2007/0243497 A1 | 10/2007 | Voudouris |
| 2007/0248926 A1 | 10/2007 | Lai et al. |
| 2007/0256694 A1 | 11/2007 | Kussick |
| 2007/0259301 A1 | 11/2007 | Hagelganz et al. |
| 2007/0264606 A1 | 11/2007 | Muha |
| 2007/0281269 A1 | 12/2007 | Forster |
| 2008/0014544 A1 | 1/2008 | Nucera |
| 2008/0128297 A1 | 6/2008 | Rose |
| 2008/0131831 A1 | 6/2008 | Abels et al. |
| 2008/0138759 A1 | 6/2008 | Kravitz et al. |
| 2008/0160474 A1 | 7/2008 | Wolf et al. |
| 2008/0182219 A1 | 7/2008 | Spalty |
| 2008/0223377 A1 | 9/2008 | Kussick |
| 2008/0227047 A1 | 9/2008 | Lowe et al. |
| 2008/0268398 A1 | 10/2008 | Cantarella |
| 2009/0004617 A1 | 1/2009 | Oda et al. |
| 2009/0004618 A1 | 1/2009 | Oda et al. |
| 2009/0004619 A1 | 1/2009 | Oda et al. |
| 2009/0042160 A1 | 2/2009 | Ofir |
| 2009/0162807 A1 | 6/2009 | Hagelganz et al. |
| 2009/0291404 A1 | 11/2009 | Oda |
| 2009/0325118 A1 | 12/2009 | Lewis et al. |
| 2010/0003632 A1 | 1/2010 | Ruiz Diaz et al. |
| 2010/0062387 A1 | 3/2010 | Hilliard |
| 2010/0129765 A1 | 5/2010 | Mohr et al. |
| 2010/0159411 A1 | 6/2010 | Oda |
| 2010/0178629 A1 | 7/2010 | Oda et al. |
| 2010/0196839 A1 | 8/2010 | Stevens |
| 2010/0196840 A1 | 8/2010 | Lai et al. |
| 2010/0203463 A1 | 8/2010 | Huff |
| 2010/0233644 A1 | 9/2010 | Macchi |
| 2010/0261131 A1 | 10/2010 | Ruiz-Vela et al. |
| 2010/0279247 A1 | 11/2010 | Kesling |
| 2010/0285420 A1 | 11/2010 | Oda |
| 2010/0285421 A1 | 11/2010 | Heiser |
| 2010/0304321 A1 | 12/2010 | Patel |
| 2011/0014583 A1 | 1/2011 | Romano et al. |
| 2011/0020762 A1 | 1/2011 | Kanomi et al. |
| 2011/0039224 A1 | 2/2011 | Cosse |
| 2011/0076633 A1 | 3/2011 | Bryant |
| 2011/0081622 A1 | 4/2011 | Mashouf |
| 2011/0086322 A1 | 4/2011 | Baron et al. |
| 2011/0123942 A1 | 5/2011 | Rudman et al. |
| 2011/0165532 A1 | 7/2011 | Benvegnu' et al. |
| 2011/0287378 A1 | 11/2011 | Dupray et al. |
| 2012/0070797 A1 | 3/2012 | Edgren |
| 2012/0288816 A1 | 11/2012 | Dupray et al. |
| 2012/0322020 A1 | 12/2012 | Smith et al. |
| 2013/0302745 A1 | 11/2013 | Aldo |
| 2013/0309624 A1 | 11/2013 | Smith et al. |
| 2014/0205961 A1 | 7/2014 | Dupray et al. |
| 2014/0356801 A1 | 12/2014 | Smith et al. |

FOREIGN PATENT DOCUMENTS

| | | |
|---|---|---|
| EP | 0317098 | 5/1989 |
| EP | 0379668 | 8/1990 |
| EP | 0389223 | 9/1990 |
| EP | 0397533 | 11/1990 |
| EP | 0588961 | 3/1994 |
| EP | 0624354 | 11/1994 |
| EP | 0875211 | 11/1998 |
| EP | 1332727 | 8/2003 |
| EP | 1359859 | 11/2003 |
| ES | 2130174 | 7/1999 |
| FR | 2497657 | 7/1982 |
| FR | 2887135 | 12/2006 |
| JP | S60-113016 | 7/1985 |
| JP | S64-25847 | 1/1989 |
| JP | H01-160547 | 6/1989 |
| JP | H02-147112 | 12/1990 |
| JP | H03-21236 | 1/1991 |
| JP | H06-507803 | 9/1994 |
| JP | 2579431 | 2/1997 |
| JP | 11-276504 | 10/1999 |
| JP | 2003-102749 | 4/2003 |
| JP | 2009-535160 | 10/2009 |
| JP | U3155836 | 11/2009 |
| WO | WO 91/07925 | 6/1991 |
| WO | WO 92/00041 | 1/1992 |
| WO | WO 92/20296 | 11/1992 |
| WO | WO 2004/039276 | 5/2004 |

OTHER PUBLICATIONS

U.S. Appl. No. 13/919,545, filed Jun. 17, 2013, Edgren.
Official Action for U.S. Appl. No. 13/766,997 mailed Jul. 9, 2013, 14 pages.
U.S. Appl. No. 10/821,699, filed Apr. 9, 2004, Ricketts.
U.S. Appl. No. 11/123,470, filed May 5, 2005, Wilson.
U.S. Appl. No. 13/199,828, Sep. 9, 2011, Rudman et al.
U.S. Appl. No. 13/506,513, filed Apr. 23, 2012, Rudman et al.
"Direct Bond Tubes," American Orthodontics, New Products Catalog, 2005, p. 76.
"Focus on Brackets," Orthodontic Products, Mar. 2005, pp. 1-2.
3M Unitek Corporation Catalog, 1990, pp. 1-1, 1-3, 3-7, Figs. A, B.
Ricketts, "Provocations and Perceptions in Cranio-Facial Orthopedics," RMO, Inc., Denver, CO, USA, 1989, cover and pp. 982-1021.
Ortho Organizers, Inc. Advertisement, "Journal of Clinical Orthodontics," Sep. 1989, 3 pages.
Epstein, "Bi-Dimensional Orthos Treatment: Benefits and Rationale of Differential Bracket-Slot Sizes," Clinical Impressions, 1998, vol. 7(3), 6 pages.
"Buccal Tube," Sankin, printed Apr. 1, 2004, 7 pages.
Victory Series Appliance System, Mastering the Art of Orthodontic Application, 3M Unitek Dental Products Division, 1998, 4 pages.
International Search Report for International (PCT) Patent Application No. PCT/US03/34430, mailed May 24, 2004.
International Search Report for International (PCT) Patent Application No. PCT/US11/38229, mailed Sep. 21, 2011 2 pages.
Written Opinion for International (PCT) Patent Application No. PCT/US11/38229, mailed Sep. 21, 2011 4 pages.
Official Action for U.S. Appl. No. 11/782,569, mailed Mar. 10, 2010.
Official Action for U.S. Appl. No. 11/782,569, mailed Oct. 12, 2010.
Notice of Allowance for U.S. Appl. No. 11/782,569, mailed Jan. 25, 2011.
Official Action for U.S. Appl. No. 13/117,085, mailed Dec. 13, 2011 17 pages.
Official Action for U.S. Appl. No. 13/117,085, mailed Mar. 28, 2012 22 pages.
Official Action for U.S. Appl. No. 13/117,070, mailed Dec. 13, 2011 13 pages.
Official Action for U.S. Appl. No. 13/117,070, mailed Mar. 22, 2012 7 pages.
Notice of Allowance for U.S. Appl. No. 13/117,085, mailed Oct. 18, 2012 13 pages.

(56) References Cited

OTHER PUBLICATIONS

U.S. Appl. No. 14/049,730, filed Oct. 9, 2013, Smith et al.
International Preliminary Report on Patentability for International (PCT) Patent Application No. PCT/US11/38229, mailed Nov. 21, 2013, 6 pages.
Notice of Allowance for U.S. Appl. No. 13/766,997 mailed Oct. 30, 2013, 16 pages.
U.S. Appl. No. 13/762,994, filed Feb. 8, 2013, Macchi et al.
Official Action for U.S. Appl. No. 14/223,194 mailed Jun. 26, 2014, 7 pages.
U.S. Appl. No. 14/627,137, filed Feb. 20, 2015, Dupray et al.
U.S. Appl. No. 14/658,781, filed Mar. 16, 2015, Gualano.
Extended Search Report for European Patent Application No. 11865141.3, dated Jan. 14, 2015 6 pages.
English Translation of Official Action for Japan Patent Application No. 2014-510291, mailed Feb. 24, 2015 3 pages.
Notice of Allowance for U.S. Appl. No. 14/223,194, mailed Oct. 14, 2014 7 pages.

\* cited by examiner

ORTHODONTIC APPLIANCE WITH ENCODED INFORMATION

REFERENCE TO RELATED APPLICATIONS

The present application is a continuation of U.S. patent application Ser. No. 13/117,070, filed May 26, 2011, which is a continuation-in-part of U.S. patent application Ser. No. 11/782,569, filed Jul. 24, 2007 (now U.S. Pat. No. 7,959,437), which is a continuation-in-part of U.S. patent application Ser. No. 10/848,929, filed May 18, 2004 (now U.S. Pat. No. 7,247,018), which is a continuation-in-part of U.S. patent application Ser. No. 10/284,016, filed on Oct. 29, 2002 (now U.S. Pat. No. 6,846,178), all of which are also incorporated herein by this reference.

FIELD OF THE INVENTION

This invention generally relates to edgewise orthodontic brackets and, more particularly, to edgewise brackets having enhanced treatment, comfort and ease-of-use features, as well as increased modalities and a character base.

BACKGROUND OF THE INVENTION

Orthodontic brackets are widely used to align teeth through the application of forces selectively provided by interconnected archwires and accessories. Brackets are typically of metal, ceramic or composite construction and are interconnected to either bands or bonding pads for attachment to teeth.

In edgewise brackets, an archwire passes through a labially opening, horizontal slot defined by one or more pair of opposing tie wings. The archwire is preshaped and sized to provide the desired forces. In each bracket, a tie wing pair includes a gingivally extending tie wing and occlusally extending tie wing. Once placed in the slot of one or more pair of tie wings, an archwire is typically restricted therein by a ligating device such as a steel or elastomeric ligature.

As orthodontic treatment objectives and techniques continue to evolve, numerous corresponding edgewise bracket designs and interconnecting accessories have been proposed. Recently, it has been recognized that it is desirable to reduce frictional engagement between the archwire and bracket surfaces defining the archwire slot to facilitate space closure and bodily tooth movement. Similarly, in many situations, it is now a goal to reduce frictional engagement between the archwire and ligating device employed to restrict the archwire within the slot. Such friction reduction can markedly increase the rate of tooth movement and reduce the duration of the orthodontic treatment.

At the same time, patient comfort and ease-of-use considerations have become increasingly important. Patient comfort has been largely addressed by reducing bracket size to yield smaller and more smoothly contoured brackets. Ease-of-use considerations have stimulated bracket designs which facilitate practitioner's bracket placement/use and accommodate plural modalities.

Texturing of the lingual surface of orthodontic brackets has been used to provide improved bonding between the bracket and the tooth to which the bracket is applied. For example, U.S. Pat. No. 5,522,725, incorporated herein by reference, concerns a method of improving the bond strength of a plastic bracket by temporarily heating and then permanently deforming projections located on the base of the bracket. The deformed projections interlock with adhesive when the bracket is bonded to a tooth. U.S. Pat. No. 5,595,484, incorporated herein by reference, discloses a plastic bracket having a metal reinforcement member partly embedded in the bracket body. FIG. 13 of the '484 patent discloses a bracket base having eight recessed discontinuous portions 36 that include molded identification characters 35. U.S. Pat. No. 5,622,494, incorporated herein by reference, discloses several structures, including a spiral-like ridge, concentric rectangles, and a weave pattern. Upon being deformed, each structure creates an undercut structure for forming a mechanical bond with an adhesive. However, this patent and the other patents noted above fail to disclose a base structure that includes lettering, symbols, or numerals that are substantially continuous and that functionally serve as texturing to bond the bracket to a patient's tooth. The present invention, amongst other things as described below, addresses these shortcomings.

The present invention represents significant advances in relation to the above-noted orthodontic bracket considerations, both singularly and combinatively, while maintaining the structural integrity of the bracket.

SUMMARY OF THE INVENTION

In one aspect of the present invention, an edgewise bracket is provided having a pair of tie wings defining an archwire slot therebetween, and a pair of ligating support means, one defined within the mesial/distal extent of each tie wing. The ligating support means may be selectively employed to reduce frictional engagement between an archwire positioned in the slot and a ligating device positioned on the ligating support means and across the archwire slot. Each ligating support means includes a sloped, or angled, portion that extends labially toward the slot (e.g., labially from the gingival/occlusal periphery towards the slot), to reduce binding of a ligating device positioned thereupon. The ligating support means are preferably notches extending from the gingival or occlusal periphery of a tie wing, sized to readily receive a ligating device, and preferably having a curvlinear, concave configuration to further reduce binding. Typically, the opposing notches in a given pair of tie wings will have a common center axis which is parallel to the gingival-occlusal center axis of the bracket. When the archwire slot includes convex sidewall and/or floor portions to reduce archwire/bracket frictional engagement, the ligating support means are preferably disposed adjacent thereto (e.g., centered upon a common gingival-occlusal plane) for enhanced treatment control.

In another aspect of the present invention, an edgewise bracket is provided having a single pair of tie wings and two pairs of opposing ligating support means defined within the mesial/distal extent of the tie wings, one pair on each of the mesial and distal sides of the bracket. The gingival/occlusal extremes of the tie wings define an elliptical configuration when viewed from the labial ("viewed labially"). More particularly, each tie wing comprises central, mesial and distal portions which extend gingivally or occlusally, with ligating support means defined between the central and mesial portions and between the central and distal portions, wherein the gingival/occlusal edges of such portions define an elliptical configuration. Such configuration accommodates size reduction, yielding patient comfort benefits, while preserving structural integrity and performance.

In this regard, and as will become apparent, a single pair of opposing T-shaped tie wings is preferred. That is, the "caps" of the T-shaped tie wings define an archwire slot therebetween, and the "center legs" of each tie wing extends gingivally or occlusally. The ligating support means are preferably notches defined on the gingival/occlusal periphery on both the mesial and distal sides of a center leg of each T-shaped tie wing. The center legs each comprise a gingivally/occlusally extending cantilevered portion that can be conveniently employed as a stanchion for ligature interconnection. The mesial/distal tie wing tip portions on the outside of each notch also comprise gingivally/occlusally extending cantilevered portions that extend a sufficient distance outward from the outer tie wing sidewalls to retain a ligating device in an arcuate seat formed under the cantilevered tie wing tip portions and center legs during conventional ligation. Relatedly, the cantilevered center leg of each T-shaped tie wing should extend at least approximately the same distance outward beyond the outer gingival/occlusal extremes of the adjacent ligating support means so as to retain a ligating device when the ligating support notches are selectively employed by a practitioner to support a ligating device.

In a further aspect of the present invention, an edgewise bracket is provided having a single pair of tie wings defining an archwire slot therebetween, and an integral T-shaped hook extending gingivally/occlusally (typically only gingivally) from one tie wing, and in perpendicular relation to the longitudinal center axis of the archwire slot, wherein traction devices (e.g., rubber bands, springs, etc.) can be readily attached from a plurality of directions so as to accommodate plural modalities for treatment. The T-shaped hook is centered upon the gingival-occlusal center axis of the bracket, and is preferably provided as a cantilevered extension of the center leg of a T-shaped tie wing so as to communicate external force moments created by inter-connected traction devices close to a tooth's root center of resistance. Preferably, the T-shaped hook is generally flat as viewed from the mesial and distal aspects. Further, as viewed from the labial aspect, the T-shaped hook preferably comprises a tapered portion contiguous to the center leg of the T-shaped tie wing, an arcuate neck portion contiguous thereto, and a head portion contiguous thereto the tapered portion, wherein a traction device may be reliably maintained in the neck portion. That is, the tapered portion serves to restrict movement of the traction device towards the archwire slot of the bracket, and the head portion serves to restrict disconnection of the traction device from the T-shaped hook. The integral T-shaped hook preferably comprises a malleable material so as to allow for selective pivotal movement of the T-shaped hook by the orthodontic practitioner as may be desirable for soft tissue clearance and patent comfort.

In yet another aspect of the present invention, an edgewise bracket is provided having at least one pair of tie wings defining an archwire slot therebetween, wherein when viewed from mesial/distal aspects, the gingivally/occlusally facing outer sidewalls of the tie wing pair define a trapezoid (although rounded and/or curved sidewalls are also contemplated). One outer sidewall is disposed at an angle relative to the longitudinal center plane of the archwire slot, wherein the sidewall extends labially away from such center plane. The other sidewall is disposed substantially parallel to the archwire slot center plane. The angled sidewall is typically disposed gingivally in both maxillary and mandibular applications. By way of example, use of the described configuration and positioning allows for enhanced, early treatment of partially erupted upper bicuspids, wherein the archwire slot will be acceptably, gingivally positioned upon full eruption of the bicuspid. This enhances treatment and reduces demands upon the practitioner time. Further, bracket systems of this design will generally reduce bracket/tooth contact between the upper and lower arches. Bracket profile and strength can also be acceptably maintained using the described configuration. The benefits associated with this trapezoidal configuration may be extended to orthodontic treatment applications requiring positive, negative, or no torque by appropriately configuring/contouring the occlusal/gingival extent of the bracket base or bottom.

In another aspect of the present invention, an edgewise bracket is provided having one tie wing pair defining an archwire slot therebetween and at least one auxiliary slot extending from a gingival edge to the occlusal edge, or vice versa, wherein the slot and shaft of the auxiliary device to be inserted into the slot have complimentary configurations to restrict rotational movement therebetween. By way of example, the auxiliary slot may have adjoining flat inner sidewalls (e.g., defining square corners), and the auxiliary shaft may have complimentary flat outer sidewalls (e.g., defining square corners), wherein rotational movement therebetween is desirably restricted.

In a related aspect of the present invention, an edgewise bracket is provided having a single tie wing pair defining an archwire slot therebetween, at least one convex portion extending labially and transversely across the floor of the archwire slot, and at least one auxiliary slot extending gingivally/occlusally and positioned under the convex slot floor portion. By positioning the auxiliary slot under the convex slot floor portion, bracket height can be advantageously conserved, and therefore reduced, so as to enhance patient comfort. When two convex slot floor portions are provided, one on each of the mesial/distal sides, twin auxiliary slots may be advantageously positioned so that one passes under each of the convex slot floor portions. In addition to the above-noted advantages, this bracket yields significant tooth rotation capabilities. For example, in early treatment stages, the twin auxiliary slots can be utilized with a steel ligature to achieve rapid gross tooth rotation. As can be appreciated, complementary auxiliary slot/auxiliary shaft configurations of the above-described nature can also be employed.

In one embodiment of the present invention, an edgewise bracket is provided having a single set of opposing T-shaped tie wings with ligating support notches defined on each side (i.e., mesially and distally) of the center leg of each tie wing. The sidewalls defining the archwire slot are provided to present two sets of opposing convex sidewall portions, one set on each of the mesial and distal sides of the bracket. Similarly, the floor of the archwire slot is provided to present two convex portions extending labially and transversely across the slot, one on each of the mesial and distal sides of the bracket. By virtue of this arrangement, the bracket yields desirable tooth rotation and alignment capabilities with reduced archwire/archwire slot frictional engagement and selectively reduced archwire/ligating device frictional engagement. Further, this configuration defines a dynamic archwire slot, wherein the archwire is allowed to maintain a "memory" of its slot entry angle, as is now desirable. The notches each comprise a portion that extends labially outwardly from the gingival/occlusal periphery towards the archwire slot and presents concave, curvlinear surfaces to reduce ligature binding. The gingival/occlusal edges of the center legs and wing tip portions of the opposing T-shaped tie wings define an elliptical configuration when viewed labially so as to reduce bracket size and advance patient comfort/appearance. All prominent edges exposed to soft tissue are preferably rounded for patient comfort.

An integral T-shaped hook of the above-described nature may be optionally provided as a cantilevered gingival/occlusal extension of the center leg of either T-shaped tie wing. The T-shaped hook preferably comprises a malleable material and preferably comprises flat lingually and labially facing surfaces, wherein the hook can be manually pivoted to a limited extent by a practitioner relative to the center leg of the tie wing.

An auxiliary slot may also be optionally provided and disposed within the gingival-occlusal center plane of the bracket, underlying the center leg portions of the opposing T-shaped tie wings. Alternatively, twin auxiliary slots may be provided, one on each side of the gingival-occlusal center plane of the bracket (i.e., mesially and distally positioned), such slots passing under the mesial and the distal convex slot floor portions of the archwire slot. Whether a single or twin auxiliary slot arrangement is provided, each slot preferably has an inner-configuration which will restrict rotation of complimentary auxiliaries inserted thereto, as described above.

The T-shaped tie wings of the bracket may also be optionally defined so that the outer gingival/occlusal facing sidewalls of the tie wing pair define a trapezoid when viewed from the mesial or distal aspects. More particularly, one of the outer sidewalls is disposed at an angle relative to the longitudinal center plane of the archwire slot, and may be perpendicular to the tie wing base surface or base/bottom surface of the bracket. The other outer sidewall is disposed in parallel relation to the center plane of the archwire slot.

In combination with the above-described trapezoidal configuration, the base surface of the bracket, namely its gingival/occlusal extent, may be provided for generating "positive torque," "negative torque," and "no torque." "Positive torque" is applied to a tooth having a tooth-long axis which projects the crown outwardly from a plane which is perpendicular to the occlusal plane and which coincides with the respective arch (e.g., mandibular or maxillary) (e.g., when the tooth root is tipped lingually). "Negative torque" is applied to a tooth having a tooth-long axis which projects the crown inwardly from the above-described plane (e.g., when the tooth root is tipped buccally). "No torque" is applied to a tooth having a tooth-long axis which is properly within the above-described plane.

The configuration of the base surface of the bracket, namely its occlusal/gingival extent, may be defined in relation to a reference plane which coincides with that portion of the floor or bottom of the archwire slot which engages the archwire when positioned therein (e.g., a plane which is tangent to the two convex portions on the floor of the slot). As an example of the foregoing trapezoidal configuration and base variations, with the "angled" outer sidewall being gingivally positioned in a maxillary application, the base may be configured to generally extend from its gingival edge to its occlusal edge generally toward the noted reference plane to provide for a "positive torque" on the tooth. Moreover, the base may be configured to generally extend from its gingival edge to its occlusal edge generally away from the noted reference plane to provide for "negative torque" on the tooth. Furthermore, the base may be configured to generally extend from its gingival edge to its occlusal edge generally parallel to the noted reference plane to provide for "no torque" on the tooth. With the "angled" outer sidewall being gingivally positioned in a mandibular application, the above-described non-parallel configurations of the base would provide negative and positive torque, respectively.

The center leg of each T-shaped tie wing may also be optionally disposed at an acute angle relative to the longitudinal center axis of the slot. Such angling may be desired in applications wherein the central axis of the clinical crown is positioned at an acute angle relative to the occlusal plane in normal occlusion. Such angling correspondingly facilitates the practitioner's placement of the bracket on a tooth, wherein the axes of the center legs may be disposed along a tooth long axis, and wherein the center axis of the bracket slot may be disposed parallel to the occlusal plane. Preferably, the mesial/distal facing edges of the center leg of each T-shaped tie wing are also parallel to the axes of the center legs to further facilitate accurate placement on a tooth. It is also preferable for the center axes of opposing ligating support notches to be disposed parallel to the gingival-occlusal center plane of the bracket. Relatedly, for rotational purposes, it is preferable for the apices of the opposing convex slot sidewall portions and a convex slot floor portion correspondingly positioned on the same mesial or distal side to lie within a common plane that is disposed substantially perpendicular to the longitudinal center plane of the archwire slot.

The present invention includes a substantially continuous series of alpha-numeric characters (such as letters or numerals) or symbols (such as company logos) that are formed in a manner such that the symbols or characters on the base of the bracket serve as texturing to facilitate bonding of the bracket with the tooth when the base of the bracket is attached to the tooth using an adhesive. Hereafter, the term "characters" refers to either letters, and/or numbers, and/or graphics, and/or symbols (such as logos), and/or a combination thereof. "Substantially continuous" is meant to convey the regular matrix-like aspect of the alpha-numeric characters configured on the base so as to facilitate a more or less uniform textured surface for bonding purposes.

One of the heretofore unappreciated aspects of the present invention include the ability of a manufacturer and/or supplier of orthodontic devices to have a trademark or other identifying character (i.e., name, symbol, part number, etc.) emblazoned on the actual device. This contributes to customer confidence in purchases of "real" (vs. knock-off) products and further permits effective recalls of product in the event of later discovered difficulties.

The characters are preferably recessed, with the space between and around the characters projected. Thus, the projected space between the characters is either in contact with the tooth, or is the next surface closest to the tooth's surface if a perimeter rail is present, as discussed below. The surface of the recessed characters is preferably further away from the tooth surface than the space between the characters. Alternatively, the opposite arrangement may be used, where the space between and around the characters is recessed, and the characters themselves are projected.

In a separate aspect of the invention, a perimeter rail, and more preferably, a discontinuous perimeter rail may be used at the edge of the base. The discontinuous perimeter rail, if used, is in contact with the tooth surface, with the interior portion of the base pattern recessed relative to the surface of the discontinuous perimeter rail. If used, the perimeter rail forms a pocket to the interior of the perimeter rail that receives the adhesive. Thus, if used, a perimeter rail contacts the tooth surface, with the base pattern recessed relative to the surface of the perimeter rail.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

Figure 1A:
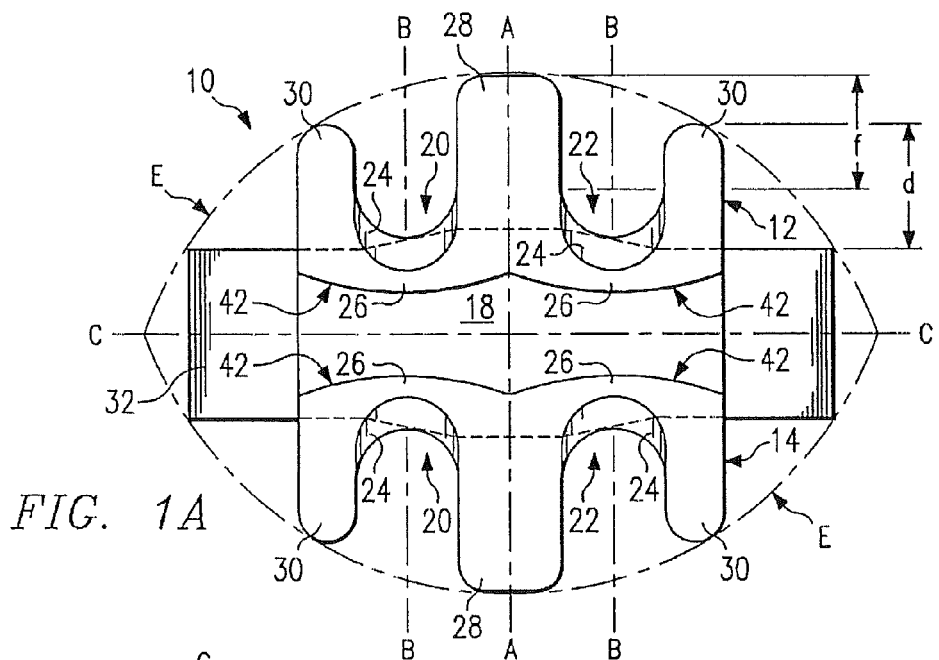
FIGS. 1A-C illustrate labial, side and end views of one embodiment of the present invention.

The drawings are not necessarily to scale.

DETAILED DESCRIPTION

One embodiment of the body of an edgewise bracket 10 of the present invention is illustrated in FIGS. 1A-C and 2A-D, with various modifications, modalities and an exemplary auxiliary reflected by FIGS. 3A-C, 4A-E, 5A-D, 6A-C and 7A-B, and with various base structures and as illustrated in FIGS. 8-18. Corresponding features are referenced by common reference numerals.

The edgewise bracket 10 comprises two integral, opposing T-shaped tie wings 12 and 14 having a common base portion and base surface 16, and defining an archwire slot 18 therebetween. By way of example only, a flange 32 may be adjoined to the bracket 10 for subsequent attachment to a band. Alternatively, the bracket may be adjoined to a bonding pad (not shown).

Two sets of opposing ligating support means 20 and 22, are provided, each set comprising a gingivally disposed notch and occlusally disposed notch on the gingival and occlusal edges of tie wings 12,14, respectively. Each ligating support means has a sloped portion 24 and top land portion 26. The sloped portions 24 have concave, curvlinear surfaces.

Each of the T-shaped tie wings 12,14 comprises a cantilevered central leg portion 28 centered upon the gingival-occlusal center axis (lying within plane AA) of the bracket 10 and cantilevered mesial/distal wing tip portions 30, with the above-noted top land portions 26 integral-therebetween. The gingival/occlusal extremes of the center leg 28 and mesial/distal wing tip portions 30 of the tie wings 12,14 define, from the labial aspect, an elliptical configuration E. In this regard, cantilevered wing tip portions 30 extend a sufficient distance d outward from the outer sidewalls 34, 36 of the tie wings 12, 14, respectively, to retain a ligating device in an arcuate seat 38 formed under the cantilevered tie wing tip portions 30 and center legs 28. Relatedly, the cantilevered center leg 28 of each T-shaped tie wing 12, 14, extends a distance f beyond the outer gingival/occlusal extreme of the ligating support means 20 adjacent thereto, such distance f being at least approximately as great as the distance d.

Figure 1C:
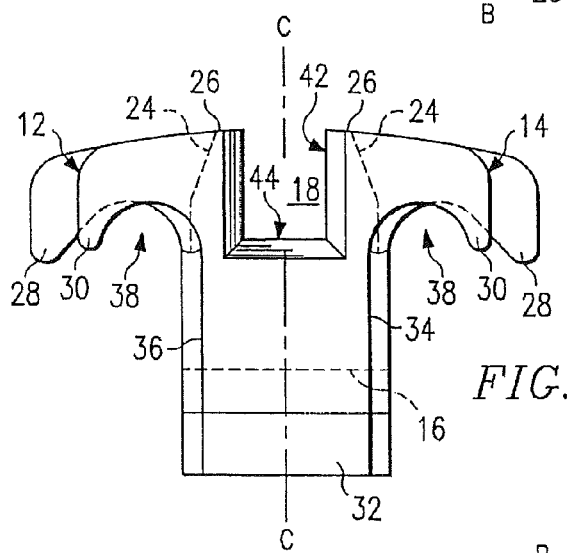
Figure 1B:
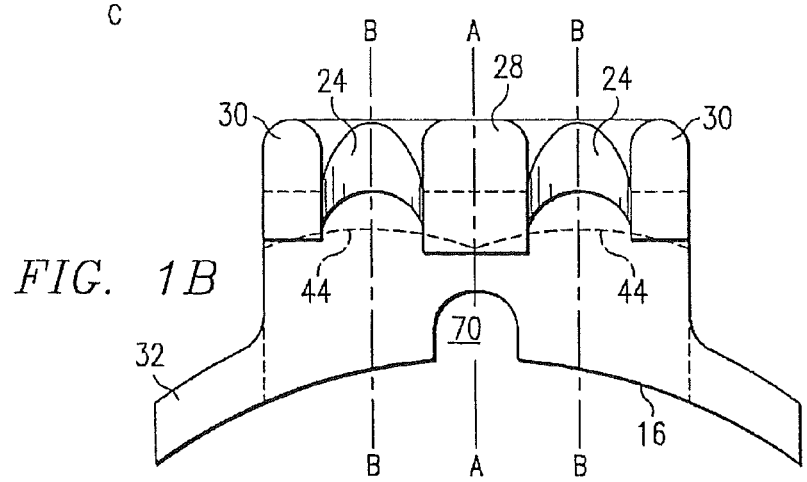

The sidewalls defining the archwire slot 18 comprise two sets of opposing convex portions 42 to reduce frictional engagement with an archwire. Similarly, the floor of archwire slot 18 is provided with two convex portions 44 extending transversely across the archwire slot 18 to reduce frictional engagement with an archwire. As illustrated in FIGS. 1A-C, the ligating support means 20, convex slot sidewall portions 42, and convex slot floor portion 44 disposed on the same side of the gingival-occlusal center plane AA may have a common center axis (lying within plane BB). As such, frictional engagement between an archwire and the slot walls and base, and between an archwire and ligating device supported on ligating support means 20 occurs in a limited region about plane BB.

Figure 7A:
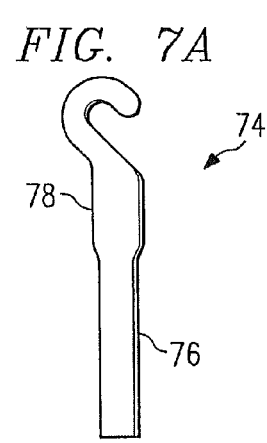
FIGS. 7A-B illustrate two views of an exemplary auxiliary device useable with the auxiliary slots of the present invention.
Figure 7B:
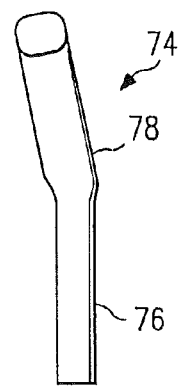

An optional auxiliary slot 70 may be provided to receive a complimentary auxiliary device, such as the exemplary auxiliary 74 illustrated in FIGS. 7A and 7B. The inner sidewalls of auxiliary slot 70 and interfacing shaft portion 76 of the exemplary auxiliary 74 are preferably configured to restrict rotational movement therebetween. As illustrated, a complimentary square-angled configuration may be employed. Additionally, the auxiliary 74 preferably comprises an extending portion 78 having an outer configuration which will not fit into auxiliary slot 70, thereby facilitating placement and removal.

Figure 2A:
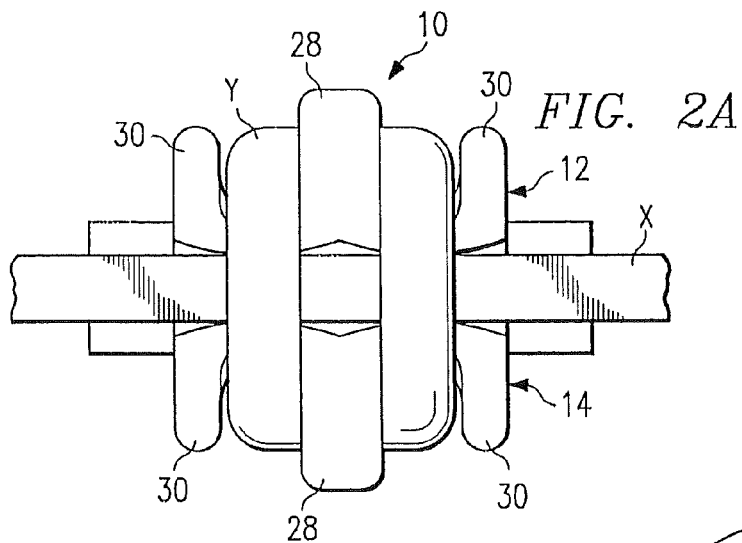
FIGS. 2A and 2B, and FIGS. 2C and 2D, illustrate labial and end views of the embodiment of FIGS. 1A-C when ligating support means are employed to support an elastomeric ligature and when ligating support means are not employed to support an elastomeric ligature, respectively.
Figure 2B:
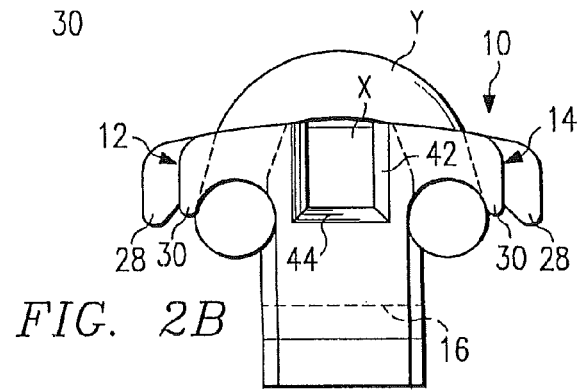
Figure 2C:
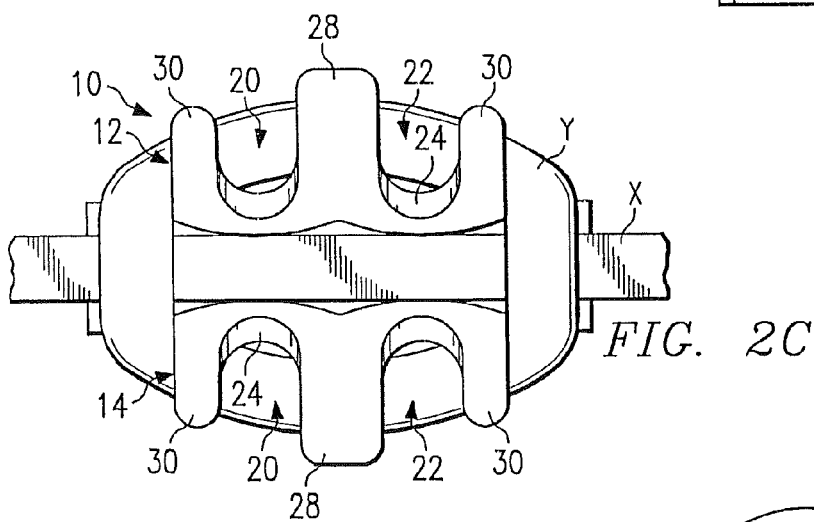
Figure 2D:
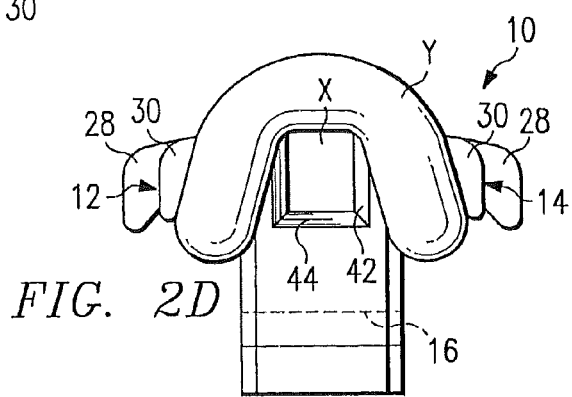

FIGS. 2A-B illustrate the interface between an archwire X and elastomeric ligating device Y when both sets of the ligating support means 20 of the embodiment of the present invention illustrated in FIGS. 1A-C are utilized. FIGS. 2C-D illustrate the interface between an archwire X and elastomeric ligating device Y when neither of the ligating support means 20 of such embodiment are utilized. As will be appreciated by those in the art, there are different treatment situations where each of these modalities may be desired. Additionally, the provision of a set of ligating support means 20 on each of the mesial and distal sides of the bracket 10 allows a practitioner to utilize one set but not the other, as may be desirable.

Figure 3A:
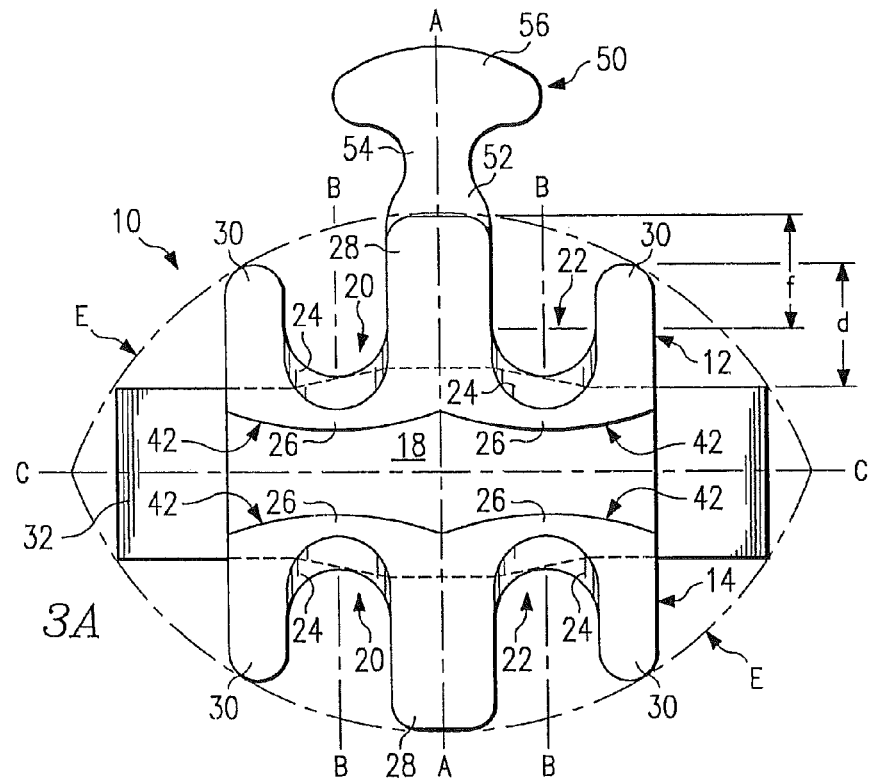
FIGS. 3A-C illustrate labial, side and end views of a modified version of said embodiment of the present invention having an integral T-shaped hook and twin auxiliary slots.
Figure 3C:
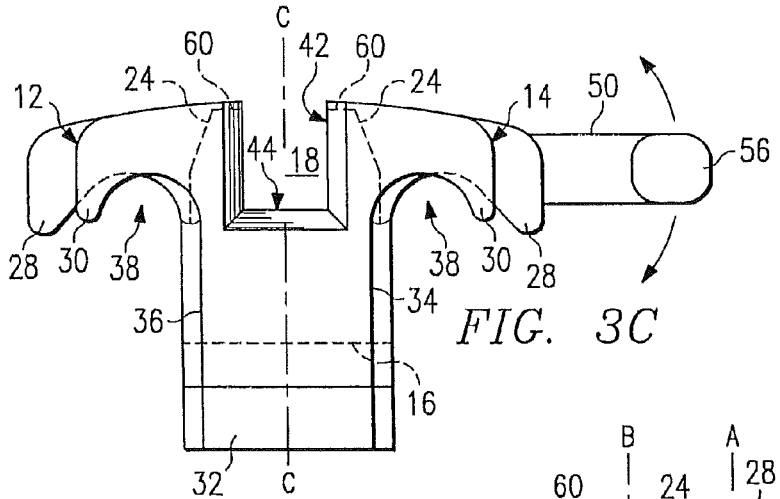
Figure 3B:
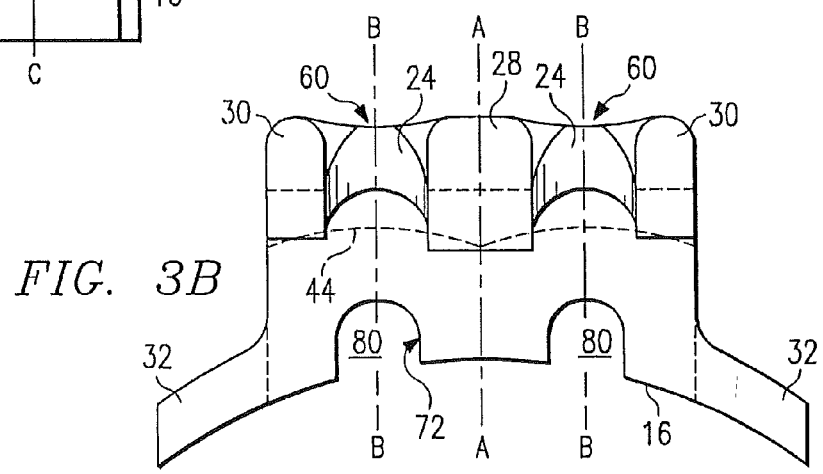

In FIGS. 3A-C an integral T-shaped hook 50 is provided as an extension to the center leg 28 of one of the T-shaped tie wings 12. The T-shaped hook 50 preferably comprises flat lingual and labial surfaces (see FIG. 3C), and is preferably malleable to allow for pivotal movement relative to center leg 20. The T-shaped hook 50 preferably comprises a tapered portion 52, arcuate neck portion 54 and head portion 56, whereby retention of a traction device in neck portion 54 is enhanced.

Twin auxiliary slots 80 may be optionally provided for receipt of an auxiliary device, such as the exemplary auxiliary 74 shown in FIGS. 7A-B. The twin auxiliary slots 80 are beneficially disposed under the convex slot floor portions 44. The configuration of slots 80 and exemplary auxiliary 74 may be as described above to restrict rotational movement therebetween and facilitate placement/removal.

FIGS. 3A-C also illustrate optional saddles 60 which can be provided in the support landing portions 26 for receiving a ligating device. It is believed that such saddles 60 may be beneficial in certain early treatment situations for purposes of retaining an undersized archwire in the desired position for rotational purposes.

In FIGS. 4A-E, the outer sidewall 34 of tie wing 12 and outer sidewall 36 of tie wing 14 define a trapezoid therebetween. Specifically outer side wall 34 is angled relative to the longitudinal center plane CC of the archwire slot 18, and the outer tie wing sidewall 36 is disposed in parallel relation to the center plane CC of the archwire slot 18. By virtue of this arrangement, the outer sidewall 34 may be, for example, advantageously disposed gingivally on partially erupted upper bicuspids. Further, bracket systems employed by this configuration will generally reduce bracket/tooth contact between upper and lower arches.

Figure 4A:
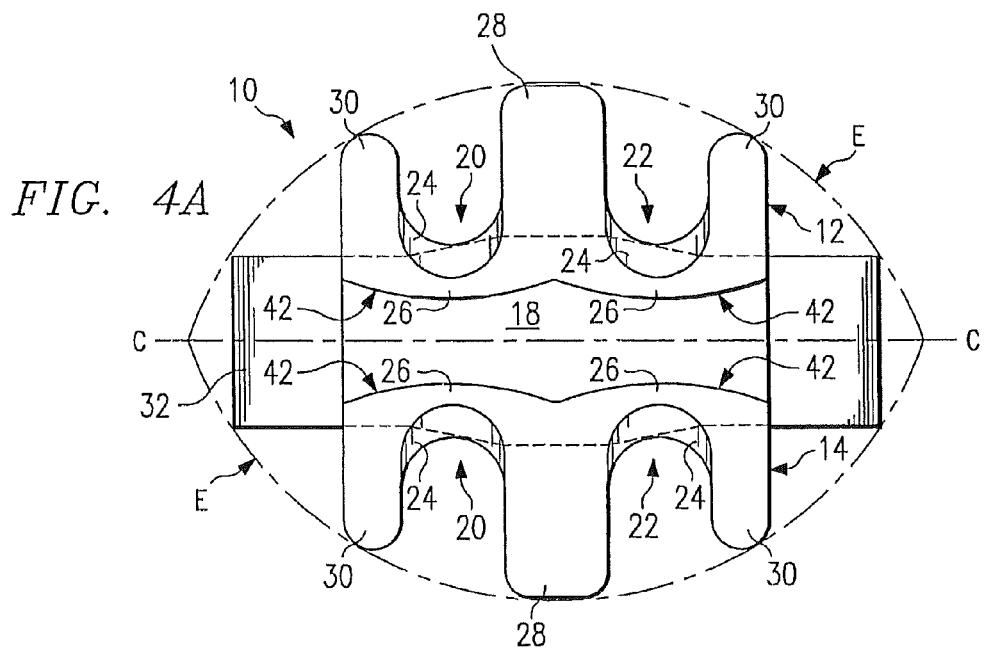
FIGS. 4A-E illustrate labial, side and end views of a modified version of said embodiment of the present invention having outer tie wing sidewalls that define a trapezoid therebetween, the end views illustrating various alternative configurations of the base to provide for positive, negative, and no torque on a tooth.
Figure 4C:
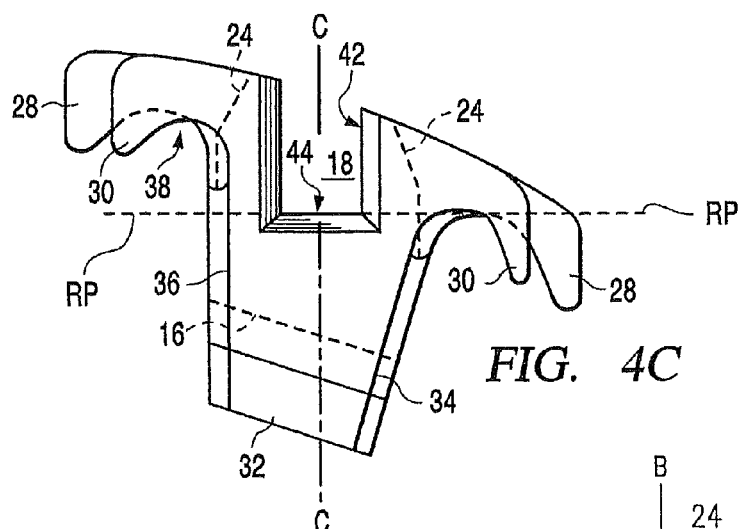
Figure 4B:
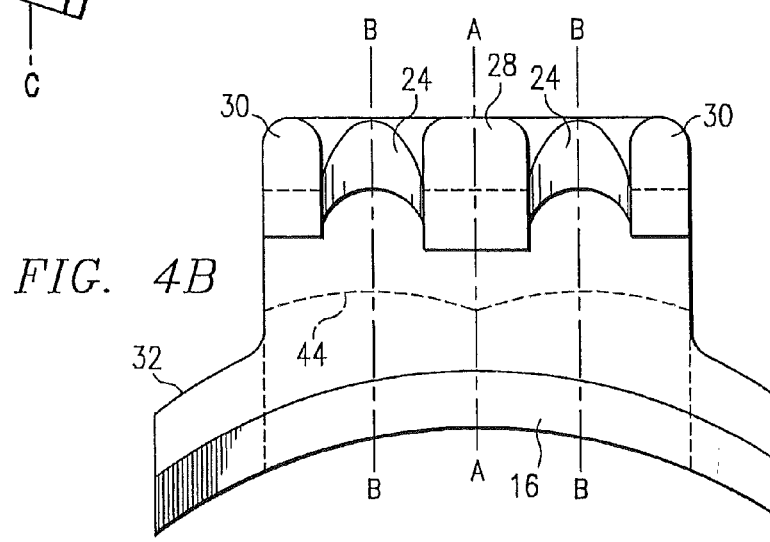
Figure 4D:
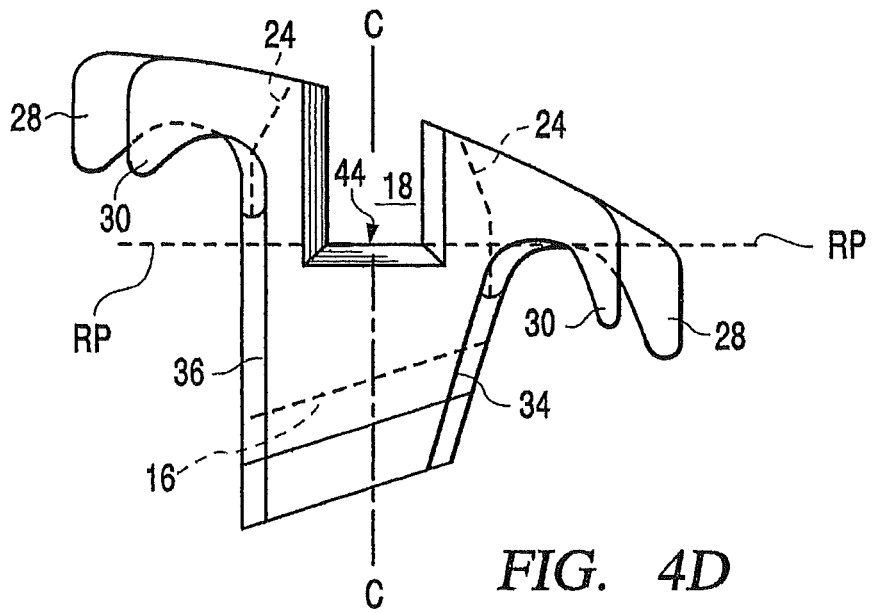
Figure 4E:
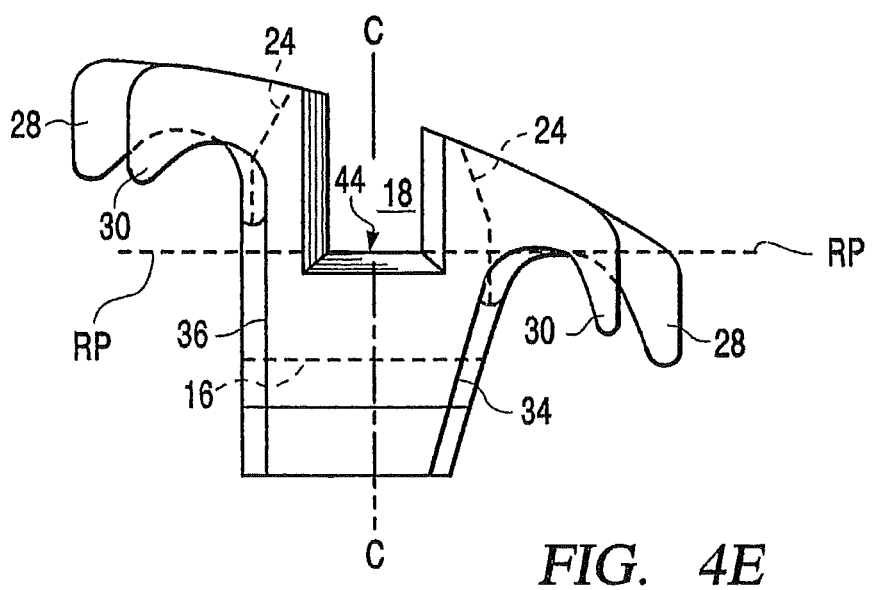

Referring in more detail to FIGS. 4C-E, the trapezoidal configuration of the bracket 10 is illustrated with three alternate configurations for the base portion 16. Generally, the configuration of the base portion 16, namely its occlusal/gingival extent, may be defined in relation to the reference plane RP. As can be seen in FIGS. 4B-E, the reference plane RP coincides with that portion of the bottom or floor of the archwire slot 18 which engages the archwire when positioned therein (e.g., a plane which is tangent to the two convex slot floor portions 44.

The configurations of base portion 16 in FIGS. 4C-E allow a practitioner to provide positive, negative, and no torque on a tooth of a particular orientation. Initially, with the tie wing 34 being gingivally positioned in a maxillary application, the base portion 16 of FIG. 4C would be used to provide for "positive torque" on a tooth, the base portion 16 of FIG. 4D would be used to provide for "negative torque" on a tooth, and the base portion 16 of FIG. 4E would be used to provide for "no torque" on a tooth. More particularly, in the case of the bracket 10 of FIG. 4C the base portion 16 would thereby extend from its gingival edge to its occlusal edge generally toward the reference plane RP in order to properly orient the archwire slot 18 on the orthodontic patient. Moreover, in the case of the bracket 10 of FIG. 4D the base portion 16 would thereby extend from its gingival edge to its occlusal edge generally away from the reference plane RP in order to properly orient the archwire slot 18 on the orthodontic patient. Furthermore, in the case of the bracket 10 of FIG. 4E the base portion 16 would thereby extend from its gingival edge to its occlusal edge generally parallel with the reference plane RP in order to properly orient the archwire slot 18 on the orthodontic patient.

In the event that the tie wing 36 is gingivally positioned in a mandibular application, the base portion 16 of FIG. 4C would provide for "negative torque" on the tooth, the base portion 16 of FIG. 4D would provide for "positive torque" on the tooth, and the base portion 16 of FIG. 4E would provide "no torque" on the tooth.

Figure 5A:
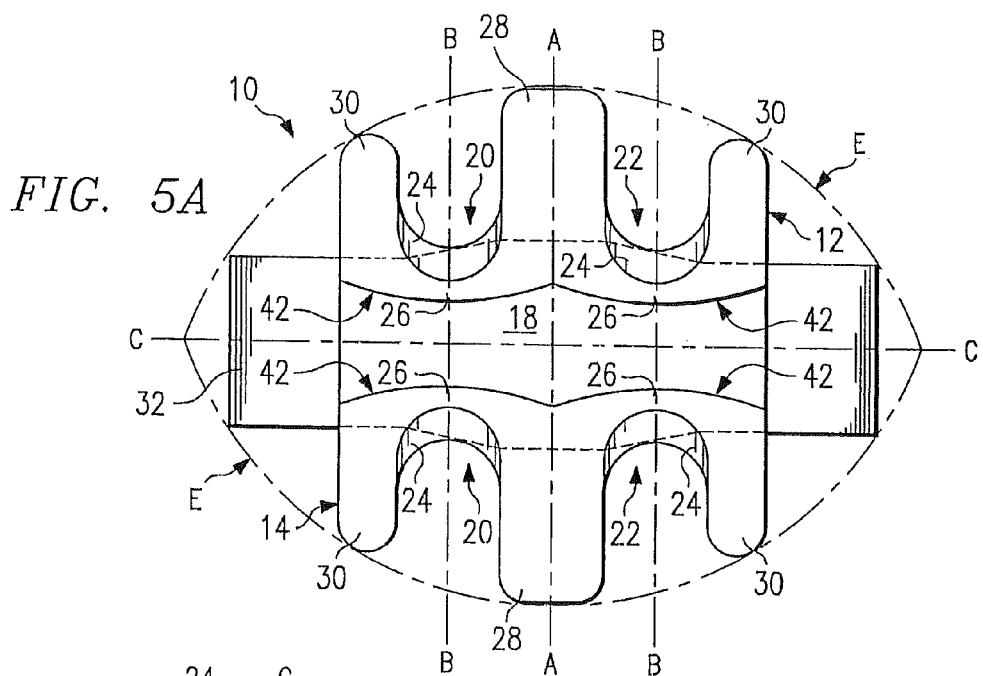
FIGS. 5A-C illustrate labial, side and end views of the modified embodiment of the present invention illustrated in FIGS. 4A-C, with a central auxiliary slot.
Figure 5C:
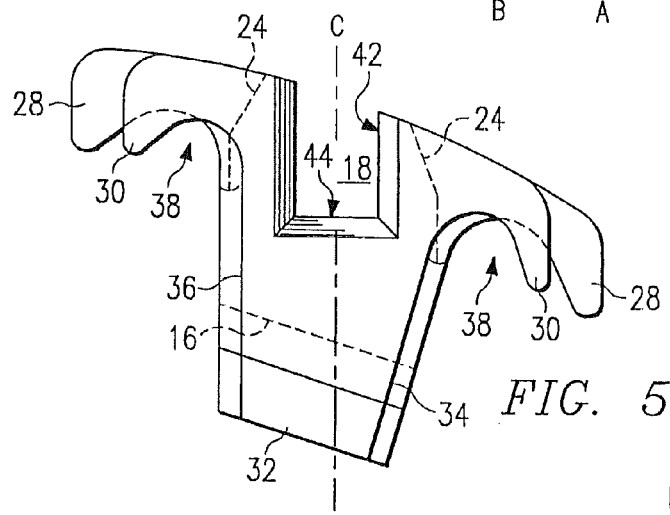
Figure 5B:
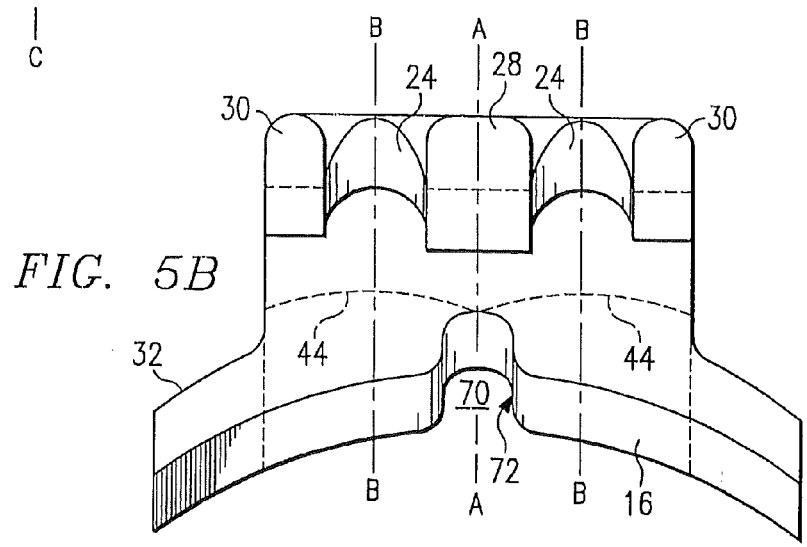
Figure 6A:
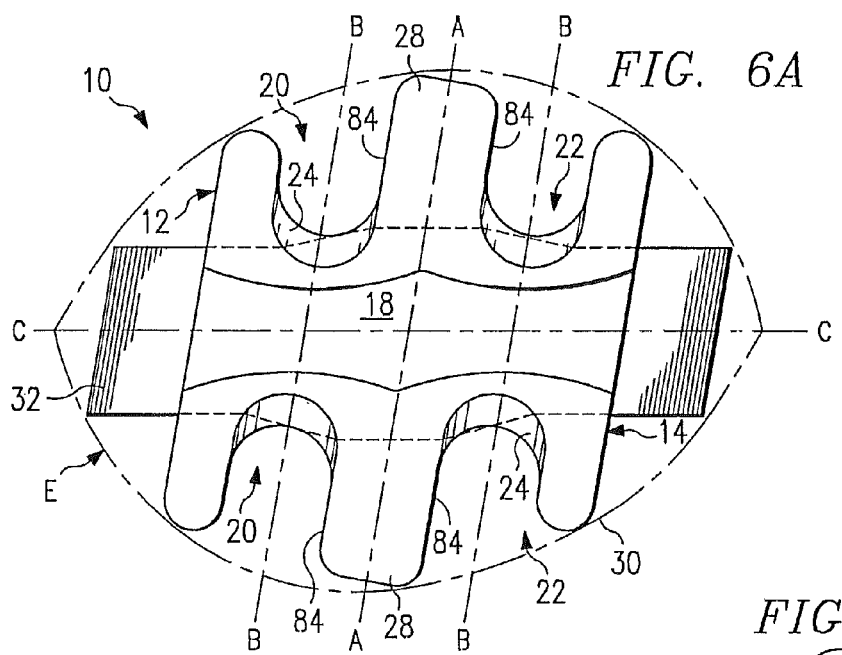
FIGS. 6A-C illustrate labial, side and opposing end views of the modified embodiment of the present invention illustrated in FIGS. 4A-C, with an angulated gingival-occlusal center axis and twin auxiliary slots.
Figure 6C:
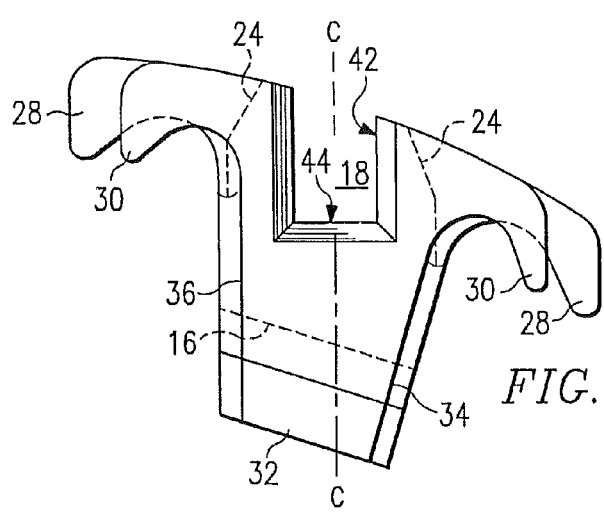
Figure 6B:
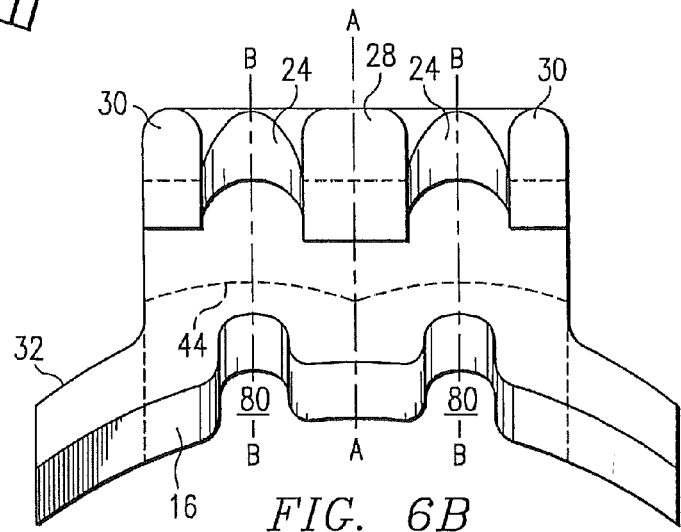

The modified embodiment illustrated in FIGS. 4A-C is shown with additional features in FIGS. 5A-C and 6A-C, although the bracket 10 of FIGS. 4D-E could be similarly modified as well. In FIGS. 5A-C, a central auxiliary slot 70 is provided. FIGS. 6A-C illustrate the inclusion of twin auxiliary slots 80 for receiving of auxiliary devices. The twin vertical slots 80 are disposed so that each passes under one of the convex slot floor portions 44.

In the version shown in FIGS. 6A-C, it should also be appreciated that the gingival-occlusal center axis of the bracket (lying within plane AA) can be disposed at an acute angle relative to center axis of archwire slot 18 (lying within plane CC). More particularly, center legs 28 may be centered upon the gingival-occlusal center axis and may be provided with distal/mesial surfaces 84 which are parallel to the gingival-occlusal center axis thereby facilitating placement of the bracket. In this modified version, it should be recognized that while the center plane BB of the ligating support means 20 is also disposed parallel to the gingival-occlusal center axis, the apices of the convex slot sidewall portions 42 and convex slot floor portion on each of mesial and distal sides lie in a plane which is perpendicular to the archwire slot center plane CC. Relatedly, it should be appreciated that, when a T-shaped hook is utilized (such as the T-shaped hook 50 illustrated in FIGS. 3A-C above), the center axis thereof will be disposed perpendicularly to the center axis of the archwire slot 18 and at an angle relative to the gingival-occlusal center axis of the bracket 10.

Figure 8:
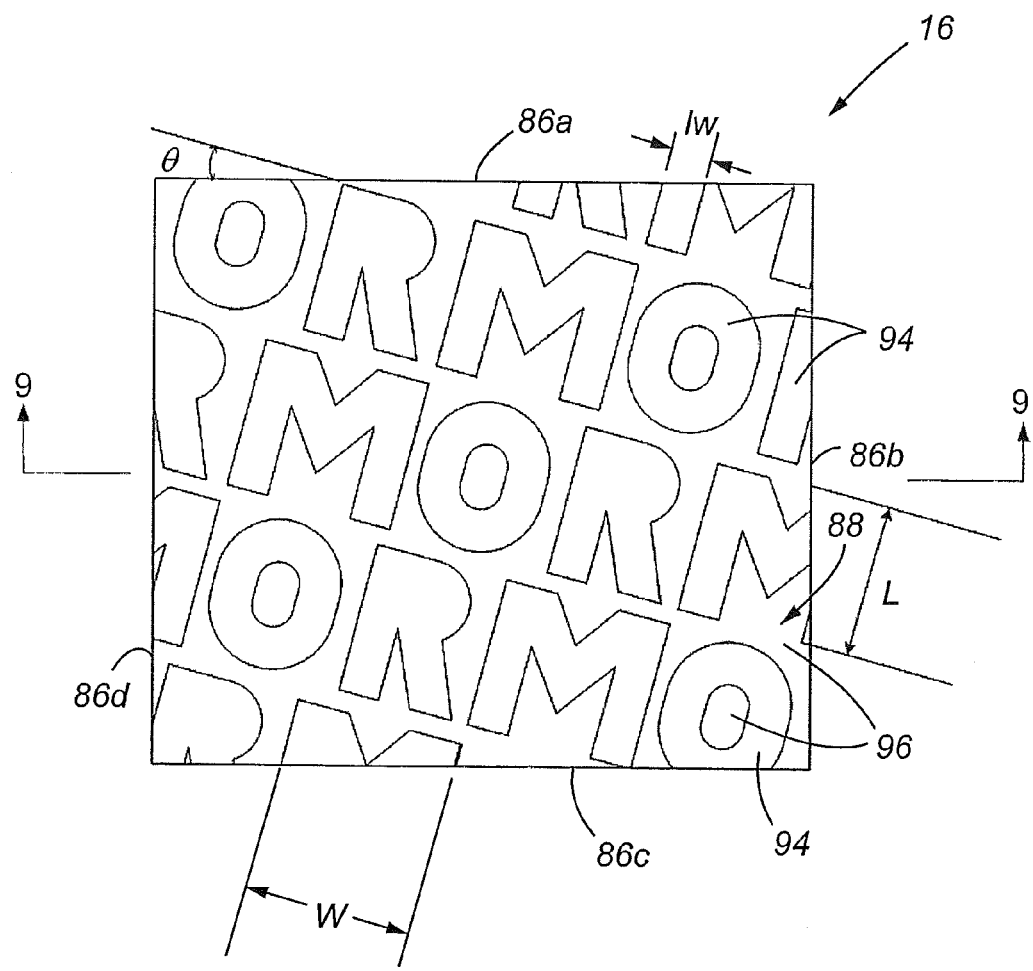
FIG. 8 is a rear view of the base of the orthodontic bracket shown in FIG. 4B without the flanges, and including a character base pattern forming an aspect of the present invention.
Figure 9A:
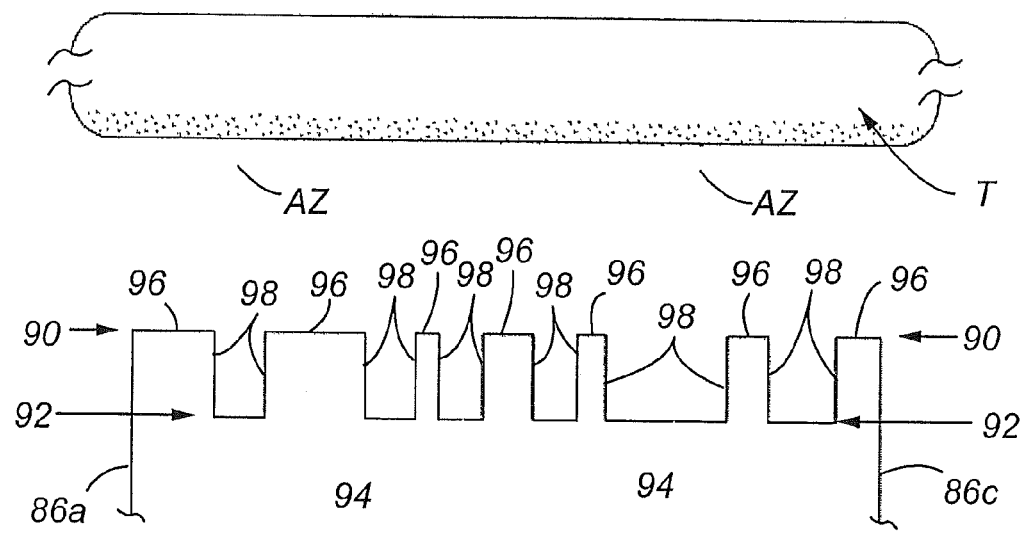
FIG. 9A-B are cross-sections taken along line 9-9 of FIG. 8.
Figure 9B:
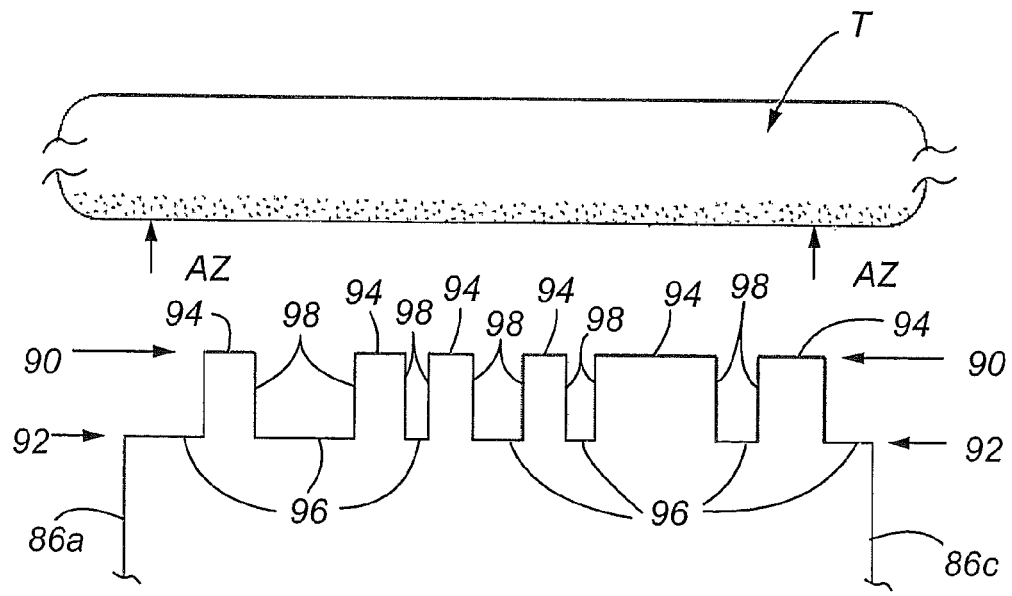

Referring now to FIG. 8, another aspect of the present invention is shown. FIG. 8 depicts an enlarged rear elevation view of the rear surface or base 16 of bracket 10, as shown in FIG. 4B, but without flanges 32. Base 16 includes gingival edge 86a, distal edge 86b, occlusal edge 86c, and mesial edge 86d. Within the interior of edges 86a,86b,86c, and 86d is interior region 88. Interior region 88 includes a projected surface 90 and a recessed surface 92, as depicted in FIGS. 9A and 9B. The projected surface 90 of the interior region 88 is a surface that is both substantially parallel to the tooth's surface and closest to the tooth's surface upon attachment of the bracket 10 to the tooth. The recessed surface 92 is a surface of the interior region 88 that is also substantially parallel to the tooth's surface, but is further away from the tooth's surface than the projected surface 90 upon attachment of the bracket 10 to the tooth. The recessed surface 92 is preferably recessed between about 0.009 to 0.011 inches relative to the projected surface 90, and more preferably, the recessed surface is recessed about 0.010 inches relative to the projected surface 90.

Characters 94 and intermediate space 96 extend substantially continuously within interior region 88, between edges 86a,86b,86c, and 86d. The pattern of characters 94 may be repeating, such as the letters "RMO" ® shown in FIG. 8, or they may be a non-repeating series of characters 94. Alternately, the characters may be a set of information regarding the bracket 10, such as its intended installation location, manufacturer, date of manufacturer, model number, etc. As one of skill in the art will appreciate, the provision of particular useful information on the base, and having such encoded information perform a useful function with respect to the use of the device, is itself a novel and nonobvious characteristic of the present invention. Regardless of the nature of the characters 94 actually used, in a preferred embodiment, the base 16 does not have a grid between the characters 94. That is, in contrast to the bracket base shown in FIG. 13 of U.S. Pat. No. 5,595,484, the base 16 of the present invention does not have a grid or lattice within which the characters reside. Rather, the present invention uses characters 94 and a relatively irregular, non-grid like intermediate space 96 to cover the entire interior region 88. The characters 94 and intermediate space 96 thus function directly as the texturing that works in combination with the adhesive to bond the bracket to the tooth.

In a separate aspect of the present invention, the characters 94 may be angled at any orientation relative to the edges 86a,86b,86c, and 86d. More specifically, the characters may be oriented parallel with edges 86a and 86c, or perpendicular to edges 86a and 86c. Likewise, the characters may be oriented parallel with edges 86b and 86d, or perpendicular to edges 86b and 86d. Alternately, the characters 94 may be oriented at an angle relative to edges 86a,86b,86c, and 86d. As an example without limitation, FIG. 8 illustrates that the characters 94 are oriented at an angle θ of about 15 degrees relative to edges 86a and 86c, and at an angle of about 75 degrees relative to edges 86b and 86d.

Character length "L" and width "W" may vary considerably. Referring now to FIG. 8, in a preferred embodiment, in plane view the length L of each characters 94 is about 0.034 to 0.038 inches, and more preferably, about 0.036 inches. The width W of each character 94 varies with the length and with the specific character type. For example, in the character string "RMO" ® shown in FIG. 8, an "M" is typically wider than an "R" or an "O".

For each character 94, the line width "lw" preferably ranges between about 0.008 to 0.010 inches, where line width lw is the width of the line forming each individual character 94. Typically, line width lw will vary with character length L. Therefore, shorter characters 94 will typically have thinner line widths lw. Obviously, logos, symbols and graphics will have lengths L, widths W, and line widths lw as required to form each individual type of shape.

The total surface area in rear elevation view, or the exterior surface of the base 16 is defined herein as the area in rear elevation view between edges 86a,86b,86c, and 86d for the base surfaces parallel to the tooth's surface. Whether the characters 94 are letters, numbers, logos, symbols, or graphics, preferably the recessed surface 92 comprises between about 50% to 60% of the total surface area of the base 16, and more preferably, about 55% of the total surface area of base 16. Correspondingly, preferably the projected surface 90 comprises between about 40% to 50% of the total surface area of the base 16, and more preferably, about 45% of the total surface area of the base 16.

Projected surface 90 and recessed surface 92 are comprised of characters 94 and intermediate space 96, which is situated between and around characters 94. Characters 94 may occupy the projected surface 90 of the base 16, but preferably occupy the recessed surface 92 of the base 16. Alternatively, intermediate space 96 may occupy the recessed surface 92 of base 16, but preferably occupy the projected surface 90 of base 16. Thus, in a preferred embodiment, upon attachment of the bracket 10 to the surface of a patient's tooth, intermediate space 96 is the projected surface 90 that is closer to the tooth surface than the characters 94 that are situated along the recessed surface 92. Separation between the characters 94 and intermediate space 96 is formed by bracket character walls 98 that are generally perpendicular or steeply sloped surfaces disposed between the characters 94 and the intermediate space 96. As shown in FIG. 9A, the projected surface 90 contacts the tooth surface upon attachment of the bracket 10 in the direction of arrows A2 to the patient's tooth T. Thus, as shown in FIG. 9A, when the intermediate space 96 occupies the projected surface 90, the intermediate surface 96 is closest to the tooth surface, and the location of characters 94 is recessed relative to the location of intermediate space 96. In contrast, FIG. 9B presents the same cross-sectional view of base 16 as that shown in FIG. 9A, but with the characters 94 and intermediate space 96 inverted. That is, in this modified arrangement, the location of intermediate space 96 is recessed relative to the location of the characters 94. Therefore, the characters 94 contact the tooth surface upon attachment of the bracket 10 in the direction of arrows A2 to the patient's tooth T.

Figure 10:
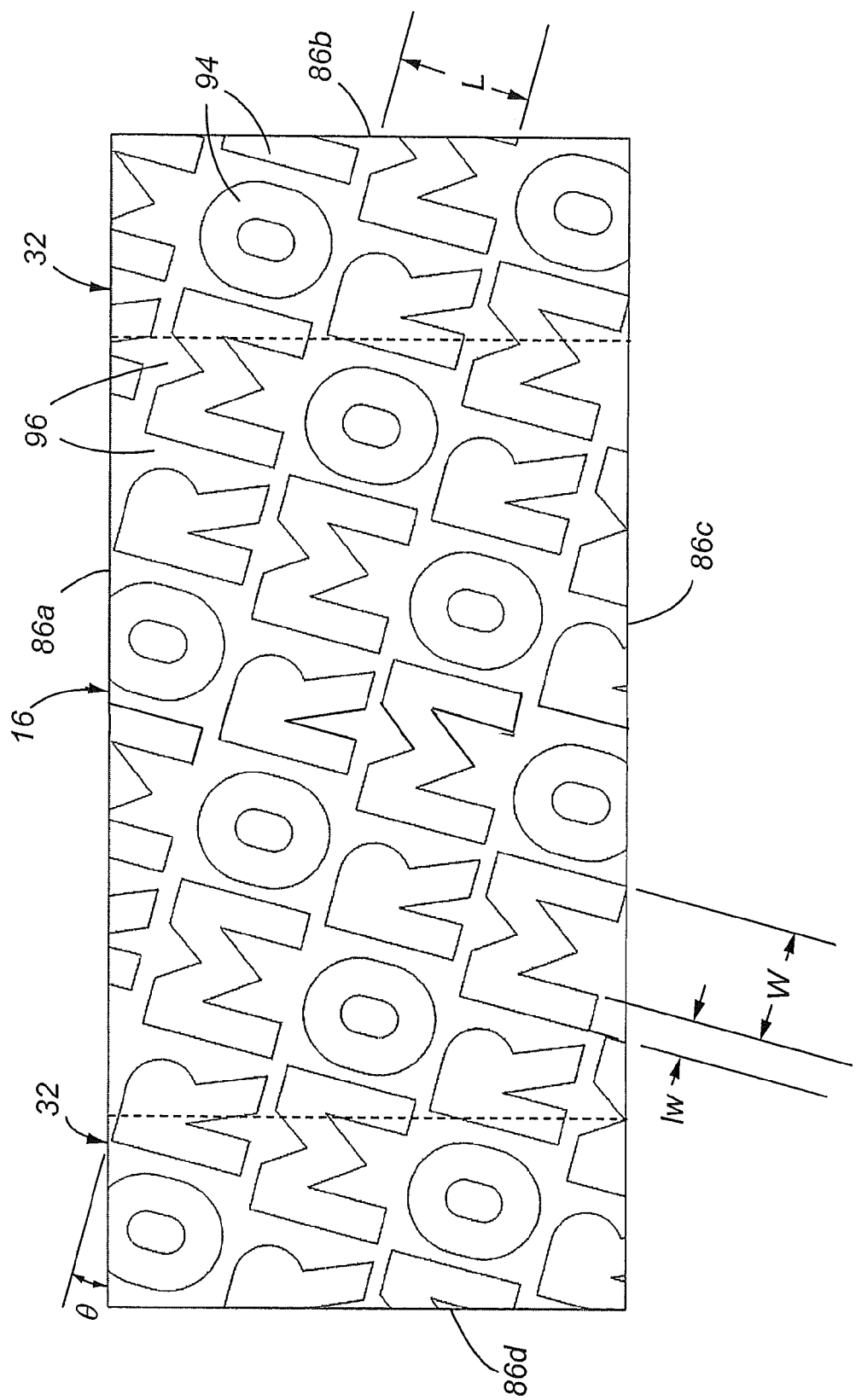
FIG. 10 is a rear view of the base of the orthodontic bracket shown in FIG. 4B with the flanges, and including a character base pattern.

Referring now to FIGS. 4B and 10, a bracket 10 with a continuous and uninterrupted base 16 and flanges 32 is shown. When flanges 32 are incorporated into the base 16 having characters 94, the characters 94 are preferably extended across the entire rear surface of the bracket 10. Preferably, the characters 94 form the recessed surface 92 as shown in FIG. 9A, and the intermediate space 96 forms the projected surface 90. Whether the characters 94 are letters, numbers, logos, symbols, or graphics, preferably the recessed surface 92 comprises between about 50% to 60% of the total surface area of the base 16 and the flanges 32, and more preferably, about 55% of the total surface area of base 16 and the flanges 32. Correspondingly, preferably the projected surface 90 comprises between about 40% to 50% of the total surface area of the base 16 and the flanges 32, and more preferably, about 45% of the total surface area of the base 16 and the flanges 32. These preferred values have been found to provide better adhesion characteristics between the bracket and the tooth to which it is applied.

Figure 11A:
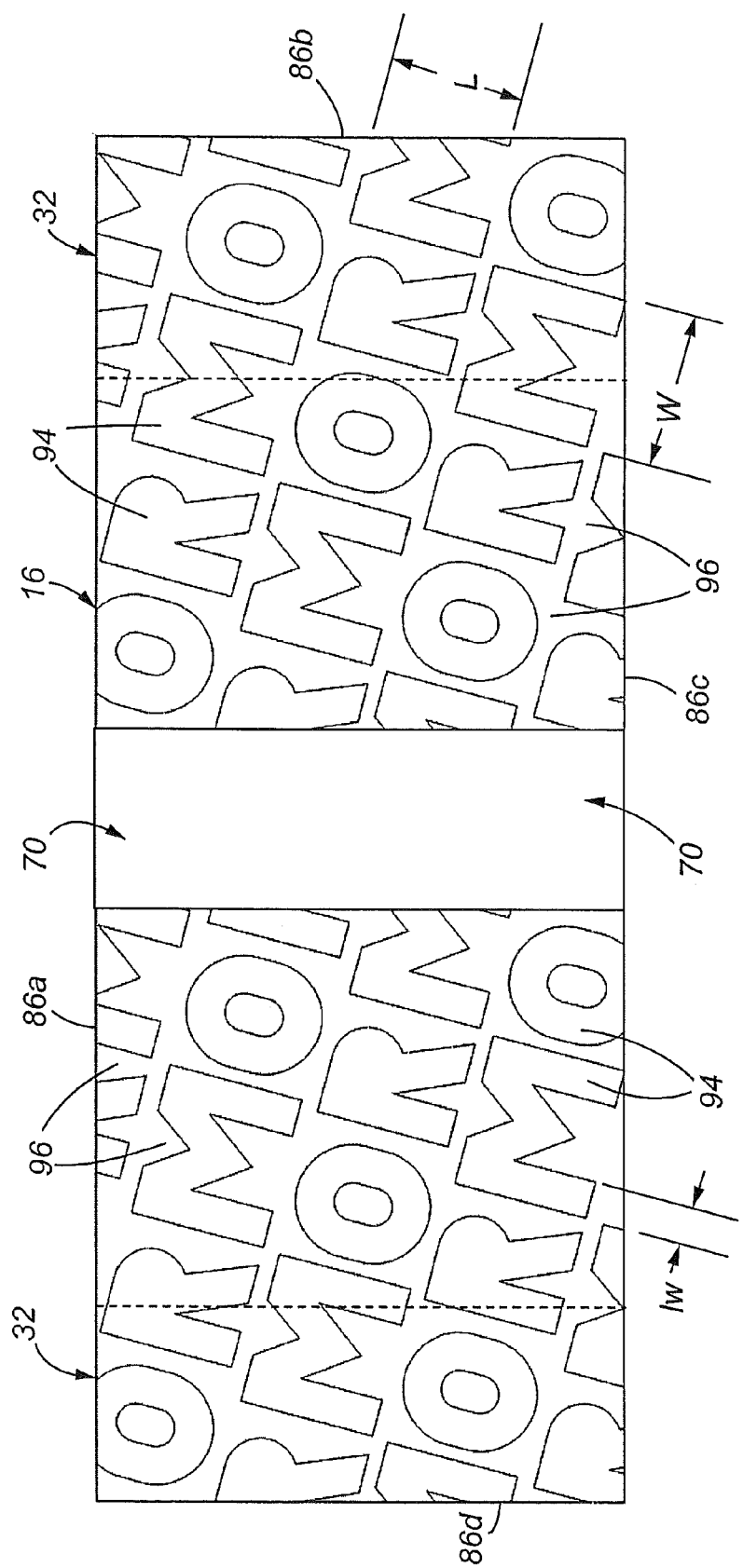
FIG. 11A is a rear view of the base of the orthodontic bracket shown in FIGS. 1B and 5B with the flanges, and including a character base pattern and an auxiliary slot without a character pattern in the auxiliary slot.
Figure 11B:
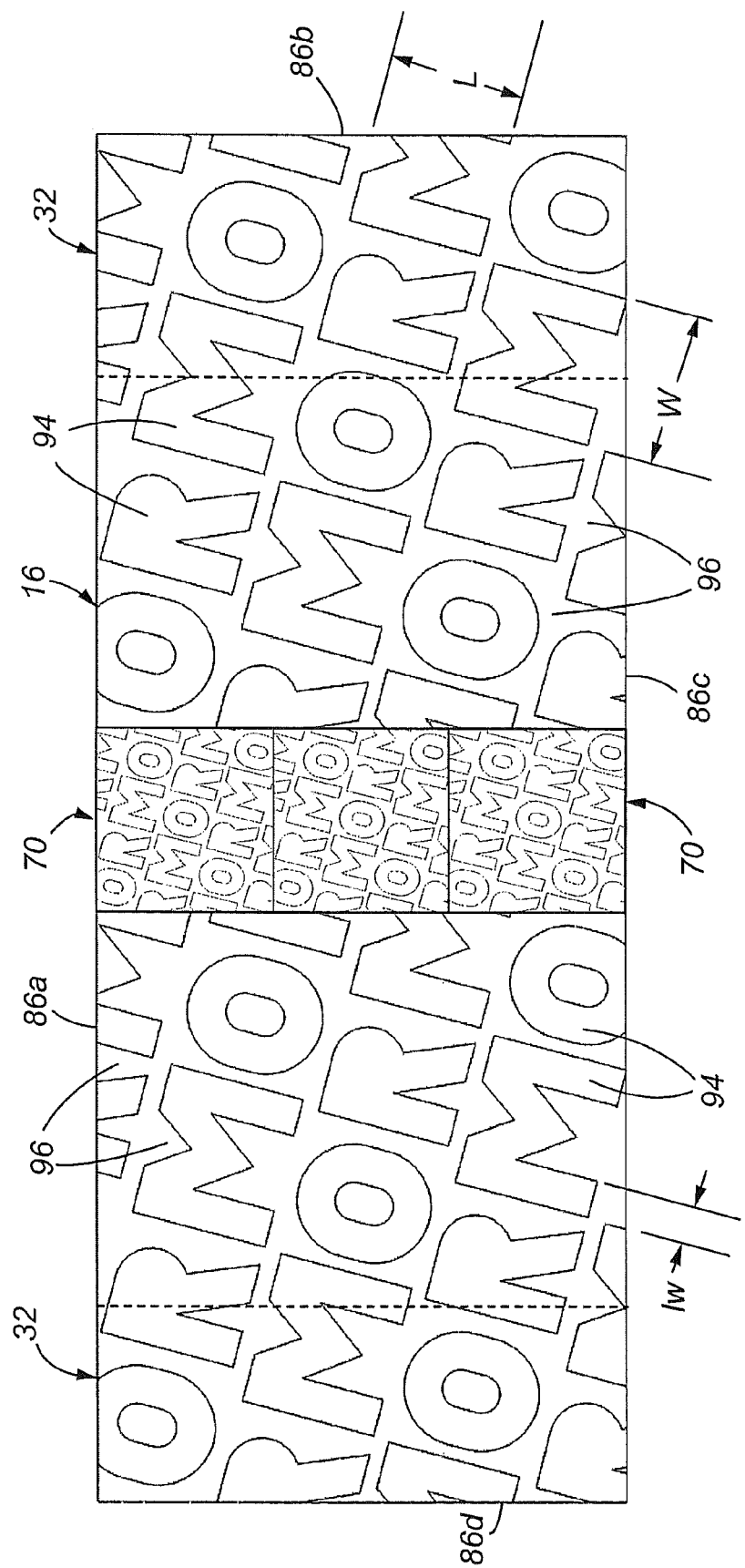
FIG. 11B is a rear view of the base of the orthodontic bracket shown in FIGS. 1B and 5B with the flanges, and including a character base pattern and an auxiliary slot with a character pattern in the auxiliary slot.

Referring again to FIGS. 1B and 5B, a bracket 10 having a base 16 with a single auxiliary slot 70 is shown. A rear plan view of the base of FIGS. 1B and 5B is shown in FIGS. 11A and 11B, wherein the rear of the bracket 10 incorporates characters 94. For the bracket shown in FIG. 11A, when flanges 32 are incorporated into the base 16 having characters 94, the characters 94 are preferably extended across the entire rear surface of the bracket 10, with the exception of the area occupied by the auxiliary slot 70. Consistent with the other embodiments described above, preferably the characters 94 form the recessed surface 92 as shown in FIG. 9A, and the intermediate space 96 forms the projected surface 90. Whether the characters 94 are letters, numbers, logos, symbols, or graphics, preferably the recessed surface 92 comprises between about 50% to 60% of the total surface area of the base 16 (not including the area occupied by the auxiliary slot 70) and the flanges 32, and more preferably, about 55% of the total surface area of base 16 (not including the area occupied by the auxiliary slot 70) and the flanges 32. Correspondingly, preferably the projected surface 90 comprises between about 40% to 50% of the total surface area of the base 16 (not including the area occupied by the auxiliary slot 70) and the flanges 32, and more preferably, about 45% of the total surface area of the base 16 (not including the area occupied by the auxiliary slot 70 and the flanges 32. These preferred values have been found to provide better adhesion characteristics between the bracket and the tooth to which it is applied.

Referring now to FIG. 11B, the bracket includes a character pattern 94 within the area of the auxiliary slot 70. When characters 94 are integrated into the auxiliary slot 70, the characters 94 may have different dimensions than that of the remaining base 16. Preferably, the character pattern 94 may be finer, thus limiting the probability of a tool to be inserted therein from hanging-up or catching on the characters 94. Alternatively, the character pattern 94 in the auxiliary slot 70 may have a rounded (not shown) or alternatively textured exterior surface that advantageously interacts with the tool to be inserted therein.

Figure 12A:
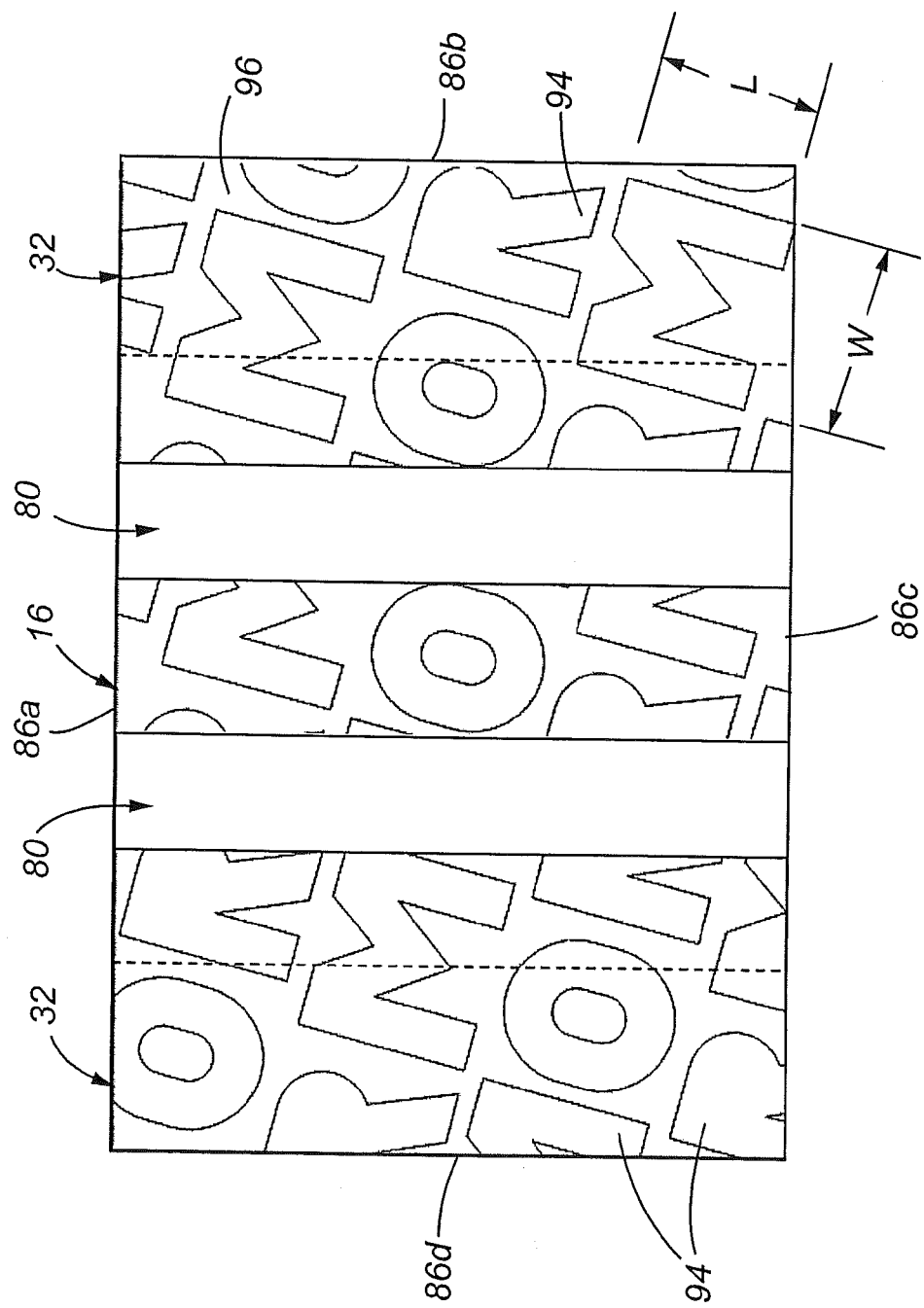
FIG. 12A is a rear view of the base of the orthodontic bracket shown in FIG. 6B with flanges, and including a character base pattern and twin auxiliary slots without a character pattern in the auxiliary slots.
Figure 12B:
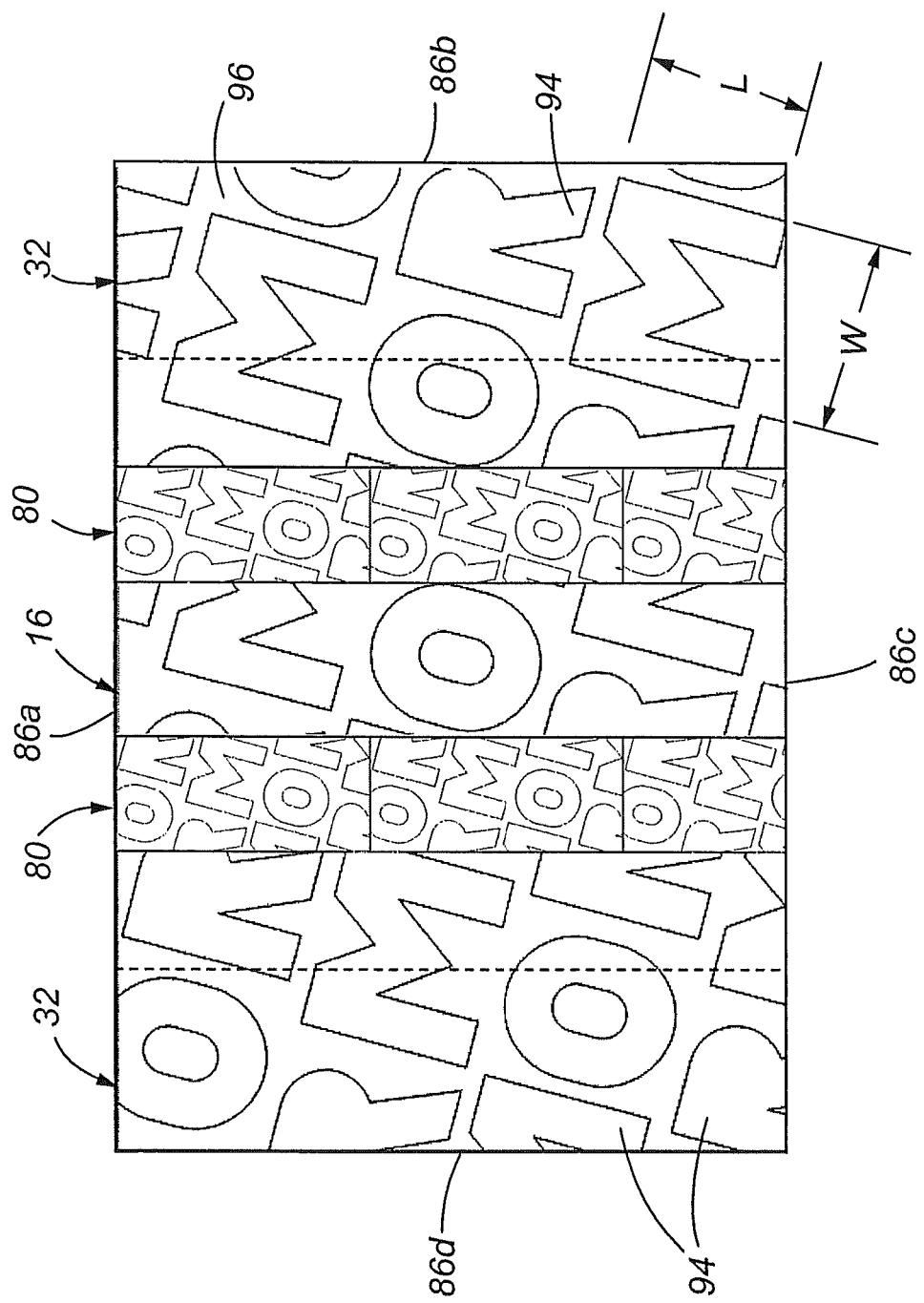
FIG. 12B is a rear view of the base of the orthodontic bracket shown in FIG. 6B with flanges, and including a character base pattern and twin auxiliary slots with a character pattern in the auxiliary slots.

Referring again to FIG. 3B, a bracket 10 having a base 16 with twin auxiliary slots 80 is shown. A plan view of the rear of FIG. 3B is shown in FIGS. 12A and 12B, wherein the rear of the bracket 10 incorporates characters 94. For the bracket shown in FIG. 12A, when flanges 32 are incorporated into the base 16 having characters 94, the characters 94 are preferably extended across the entire rear surface of the bracket 10, with the exception of the area occupied by the twin auxiliary slots 80. Consistent with the other embodiments described above, preferably the characters 94 form the recessed surface 92 as shown in FIG. 9A, and the intermediate space 96 forms the projected surface 90. Whether the characters 94 are letters, numbers, logos, symbols, or graphics, preferably the recessed surface 92 comprises between about 50% to 60% of the total surface area of the base 16 (not including the area occupied by the twin auxiliary slots 80) and the flanges 32, and more preferably, about 55% of the total surface area of base 16 (not including the area occupied by the twin auxiliary slots 80) and the flanges 32. Correspondingly, preferably the projected surface 90 comprises between about 40% to 50% of the total surface area of the base 16 (not including the area occupied by the twin auxiliary slots 80) and the flanges 32, and more preferably, about 45% of the total surface area of the base 16 (not including the area occupied by the twin auxiliary slots 80) and the flanges 32. These preferred values have been found to provide better adhesion characteristics between the bracket and the tooth to which it is applied.

Referring now to FIG. 12B, the bracket includes a character pattern 94 within the area of the auxiliary slots 80. As with the single auxiliary slot 70 shown in FIG. 11B, when characters 94 are integrated into the auxiliary slots 80, the characters 94 may have different dimensions than that of the remaining base 16. Preferably, the character pattern 94 may be finer, thus limiting the probability of a tool to be inserted therein from hanging-up or catching on the characters 94. Alternatively, the character pattern 94 in the auxiliary slots 80 may have a rounded (not shown) or alternatively textured exterior surface that advantageously interacts with the tool to be inserted therein.

Referring again to FIG. 4B, in yet a separate aspect of the invention, the bracket 10 may include a curved base 16. The base 16 may be set at a variety of angles depending upon the curvature of the patient's tooth surface.

Referring now to FIGS. 13-15A,B in yet a separate aspect of the invention, base 16 preferably includes a perimeter rail, and more preferably, a discontinuous perimeter rail. The discontinuous perimeter rail preferably includes at least one corner segment, and more preferably, a plurality of corner segments, including a distal/gingival corner 100a, a gingival/mesial corner 100b, a mesial/occlusal corner 100c, and an occlusal/distal corner 100d. Corners 100a,100b, 100c, and 100d are preferably between about 0.008 to 0.011 inches in width "cw", and more preferably, are about 0.085 inches wide. Each corner 100a,100b, 100c, and 100d is separated from the other corners segments by a distance or a cavity. Preferably, the discontinuous perimeter rail also includes at least one straight segment, and more preferably, a plurality of straight segments. More preferably yet, two straight segments are provided, namely a gingival straight segment 102a and an occlusal straight segment 102c. The gingival straight segment 102a is separated from the distal/gingival corner 100a and the gingival/mesial corner 100b by a cavity or a distance "$d_1$" of about 0.008 to 0.011 inches, and more preferably, by a distance $d_1$ approximately equal to the width cw of the discontinuous perimeter rail, or about 0.0085 inches. Similarly, the occlusal straight segment 102c is separated from the mesial/occlusal corner 100c and the occlusal/distal corner 100d by a cavity or distance $d_1$ of about 0.008 to 0.011 inches, and more preferably, by a distance $d_1$ approximately equal to the width cw of the discontinuous perimeter rail, or about 0.0085 inches. Although base 16 will function without a perimeter rail, the discontinuous perimeter rail in combination with characters 94 increases the bonding strength of bracket 10 when it is attached to a tooth using an adhesive.

Referring again to FIG. 13, although it may be present, in a preferred embodiment, the discontinuous perimeter rail does not include a distal straight segment between the distal/gingival corner 100a and the occlusal/distal corner 100d. In addition, in a preferred embodiment, the discontinuous perimeter rail does not include a mesial straight segment between the gingival/mesial corner 100b and the mesial/occlusal corner 100c.

Figure 13:
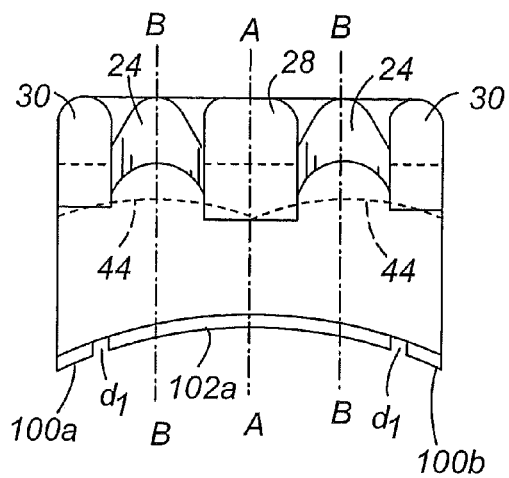
FIG. 13 is a plan view of the of the bracket of FIG. 4B without flanges, and including a discontinuous perimeter rail.
Figure 14:
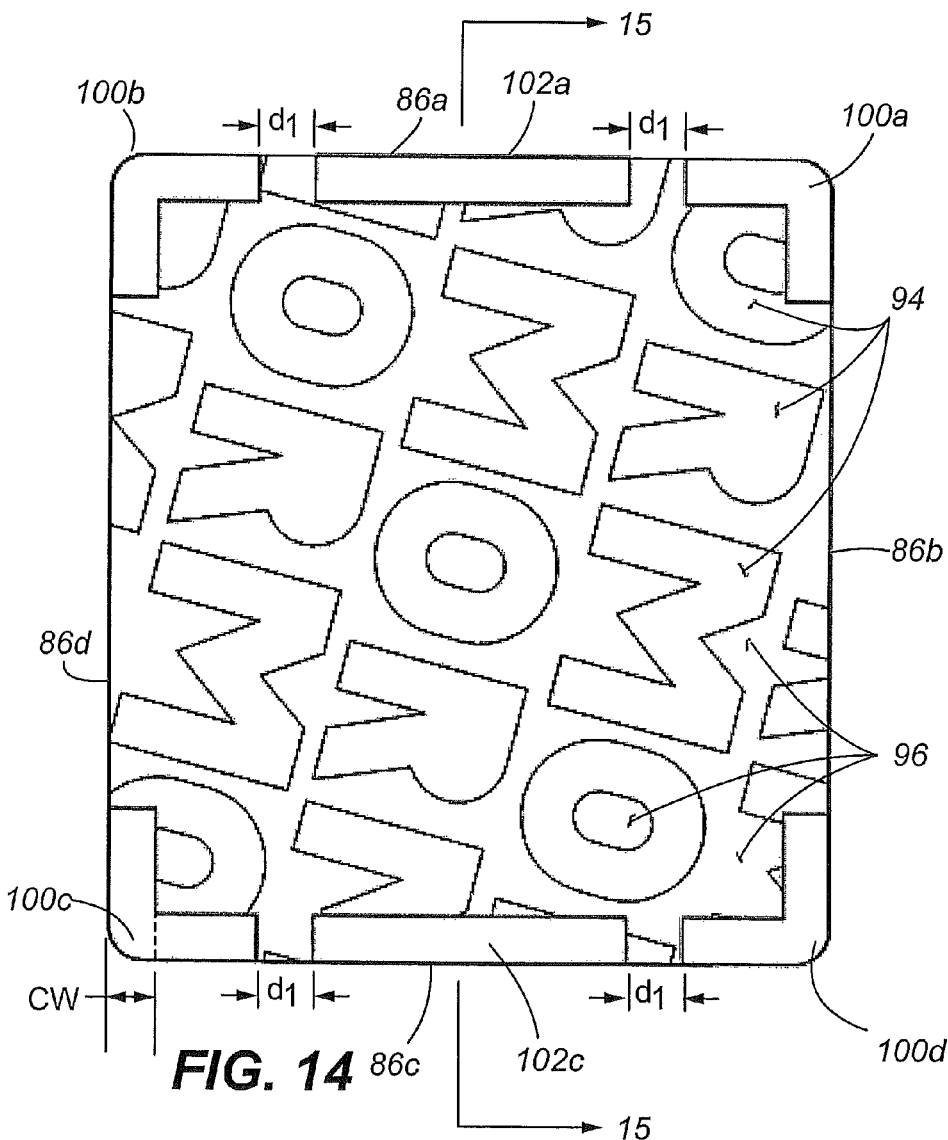
FIG. 14 is a rear view of the base of the bracket shown in FIG. 13.

Still referring to FIG. 13, in a preferred embodiment, the perimeter rail is preferably positioned within the base area defined by edges 86a,86b,86c, and 86d. More specifically, corners 100a,100b,100c, and 100d, as well as straight segments 102a and 102c of the discontinuous perimeter rail are all disposed within the interior of the area defined by base edges 86a,86b,86c, and 86d. The total surface area in rear elevation view, or the exterior surface of the base 16 is defined herein as the area in rear elevation view between edges 86a,86b,86c, and 86d for the base surfaces parallel to the tooth's surface. Where a discontinuous perimeter rail is used, the discontinuous perimeter rail portions 100a,100b, 100c, 100d, 102a and 102c comprise between about 12% to 16% of the total surface area of the base 16, and more preferably, about 14% of the total surface area of base 16. Whether the characters 94 are letters, numbers, logos, symbols, or graphics, when a discontinuous perimeter rail is present, preferably the recessed surface 92 comprises between about 45% to 50% of the total surface area of the base 16, and more preferably, about 48% of the total surface area of base 16. Correspondingly, when a discontinuous perimeter rail is present, preferably the projected surface 90 comprises between about 35% to 40% of the total surface area of the base 16, and more preferably, about 38% of the total surface area of the base 16.

Figure 15A:
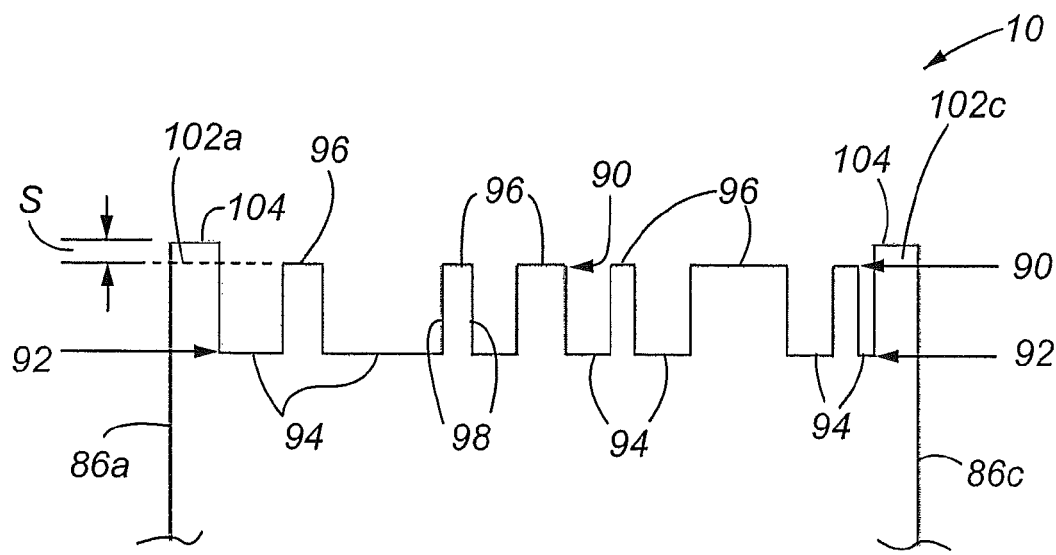
FIGS. 15A-B are cross-sections taken along line 15-15 of FIG. 14.
Figure 15B:
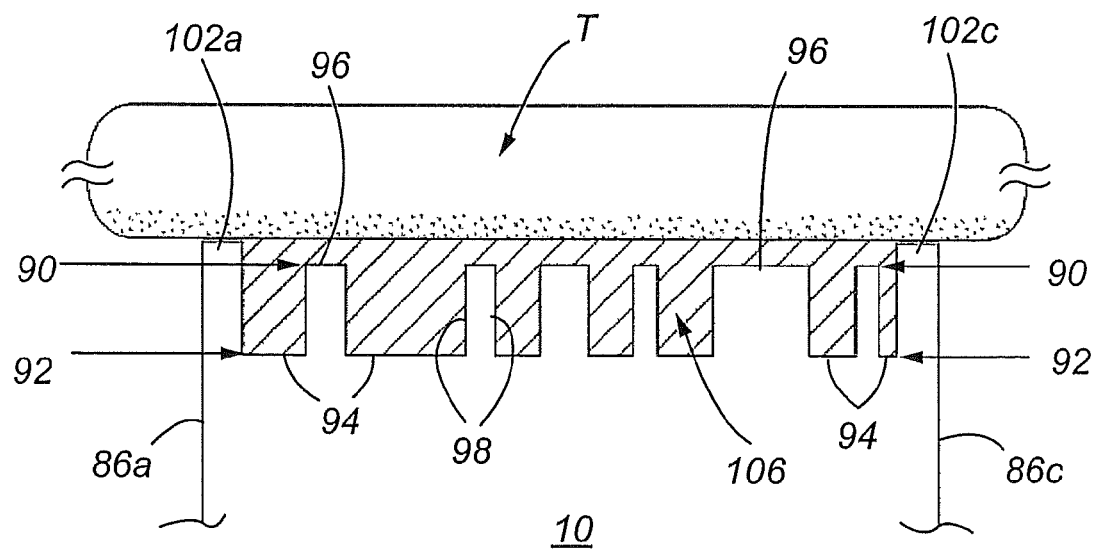

Referring now to FIG. 15A, a cross-sectional view along line 15-15 as shown in FIG. 13 is provided. The cross-sectional view of FIG. 15A shows the gingival straight segment 102*a* and the occlusal straight segment 102*c* along the gingival and occlusal edges of the bracket 10. FIG. 15A also shows that the rail surface 104 is disposed beyond the projected surface 90. In the preferred embodiment depicted in FIG. 15A, the projected surface 90 is comprised of the intermediate space 96 between characters 94, while the recessed surface 92 is comprised of the characters 94. The rail surface 104 preferably projects a distance "s" of about 0.002 to 0.004 inches beyond the projected surface 90, and more preferably, the rail surface 104 projects about 0.003 inches beyond the projected surface 90. Thus, when bracket 10 having a discontinuous rail is placed with its base 16 in contact with a patient's tooth, the rail surface 104 contacts the patient's tooth. The discontinuous rail thus forms a pocket for the collection of adhesive. Upon application of the bracket 10 to a patient's tooth, the openings between the perimeter rail permit excess adhesive to escape under the applied pressure, thereby preventing the bracket 10 from having an adhesive layer that is too thick and moving away from the tooth as a result of increased hydraulic pressure formed within the adhesive pocket when the bracket is first pressed against the tooth to which it is being applied. Thus, the discontinuous structure of the perimeter rail improves the bonding strength between the bracket and the patient's tooth because it allows excess adhesive to escape during the application of the bracket 10 to the tooth's surface. Furthermore, as shown in FIG. 15B, the difference in distance provided by the projection of the perimeter rail beyond the projected surface 90 allows a layer of adhesive 106 to bond between the projected surface 90 and the tooth's surface. Thus, a layer of adhesive is formed within the entire interior area 88 of the base that is not otherwise occupied by the discontinuous perimeter rail segments 100*a*-*d*, and 102*a* and 102*c*. This further improves bonding between the bracket 10 and the tooth's surface.

Figure 16:
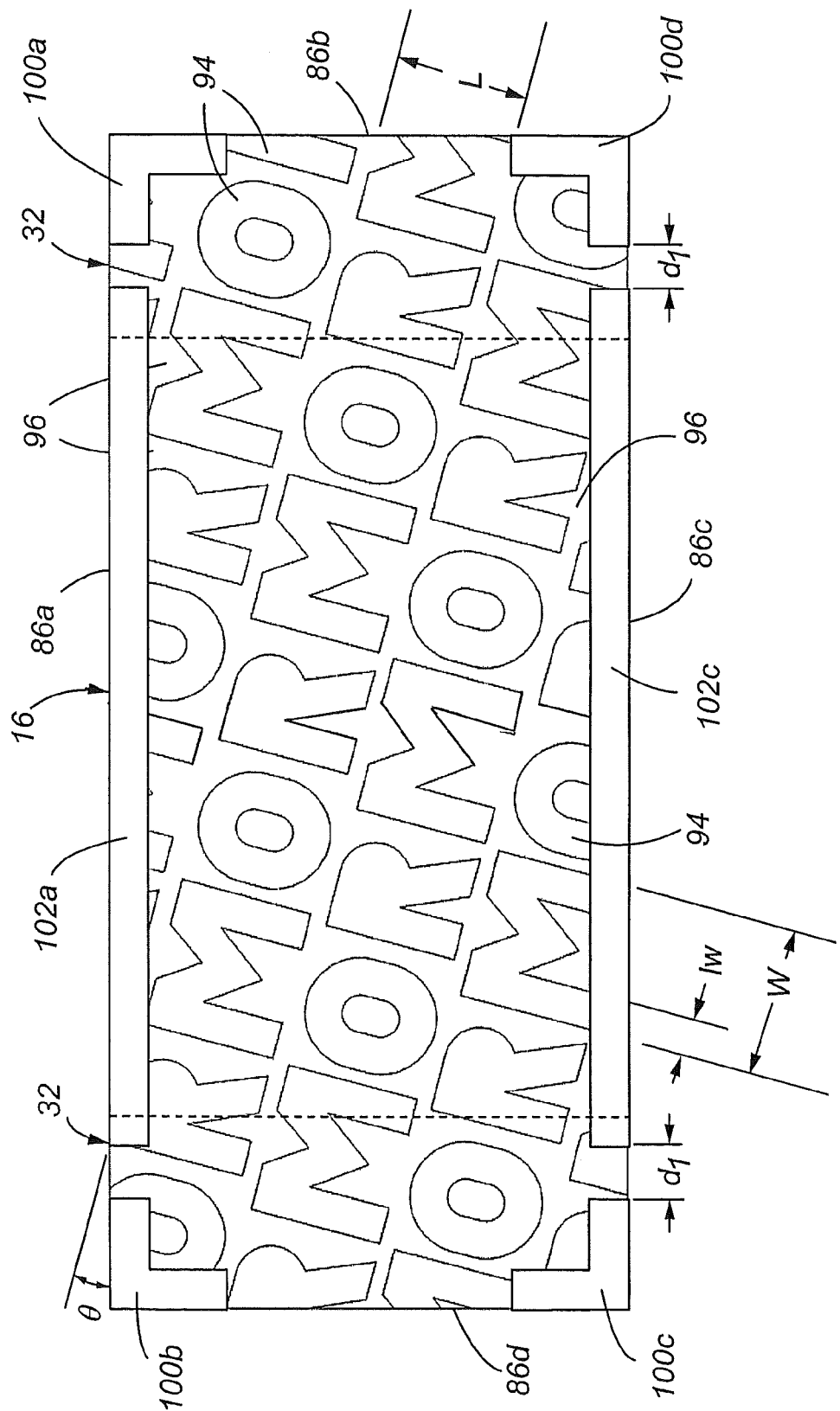
FIG. 16 is a rear view of the base of the orthodontic bracket shown in FIG. 4B with flanges, and including a character base pattern and a discontinuous perimeter rail.

Referring now to FIG. 16, for those brackets that include flanges 32 adjacent the base 16, the perimeter rail is preferably located along the outermost edges of the flanges 32. Thus, the discontinuous perimeter rail portions 100*a*,100*b*, 100*c*, and 100*d* will occupy the corners formed at the outer limits of the flanges 32. In addition, the gingival straight segment 102*a* and the occlusal straight segment 102*c* will occupy portions of the gingival edge 86*a* and the occlusal edge 86*c*, respectively. The gingival straight segment 102*a* and the occlusal straight segment 102*c* can occupy area along both the base 16 and the flanges 32, depending upon the chosen perimeter rail configuration. In addition, for those brackets that include a single auxiliary slot 70 or twin auxiliary slots 80, the perimeter rail is preferably not present along the alignment of the auxiliary slot 70 or slots 80.

In yet a separate aspect of the invention, the surface finish of the base is manufactured to provided a finish having textural characteristics suited for use with characters 94. More particularly, the present invention includes a method of making the bracket 10 and its base 16 that is specifically suited for a bracket 10 with a base 16 and flanges 32 (optional) having a continuous pattern of characters 94. In a preferred embodiment, a one-piece molded metal injected bracket 10 is manufactured from a mold 108. As known to those skilled in the art, the mold 108 is produced by electrical discharge machining using shaped electrodes to form the mold 108 itself. More specifically, the shaped electrodes are formed to correspond to the desired shape of at least a portion of one of the exterior surfaces of the bracket 10, such as the exterior surface that forms base 16. The shaped electrodes are then charged and placed in contact with a metal shape that will form a portion of mold 108 for production of the actual brackets 10. More specifically, the charged electrode "burns" the desired bracket pattern into the metal shape, thus forming a portion of mold 108. The mold is typically formed from a top and a bottom portion that is then assembled to form a hollow space that defines the bracket 10. The mold 108 is then used to manufacture a bracket 10 by injecting the mold 108 with the bracket material, such as molten stainless steel, via an injection channel that passes through mold 108 to the interior hollow region defining the bracket form. The molten stainless steel is allowed to cool and harden, and then the mold 108 is separated and molded bracket 10 is subsequently ejected from the mold 108.

In order to adequately bond the bracket 10 having a continuous pattern of characters 94 to the tooth surface using an adhesive, the surfaces of the base 16 that are parallel to the tooth's surface are preferably relatively rough. However, if the surfaces of mold 108 corresponding to the base 16 of bracket 10 are too rough, the actual bracket 10 cannot be ejected from the mold 108 during the bracket manufacturing process. Thus, in this separate aspect of the invention, the mold 108 is preferably manufactured and processed to have appropriate surficial roughness textures along its corresponding base surfaces.

Figure 17:
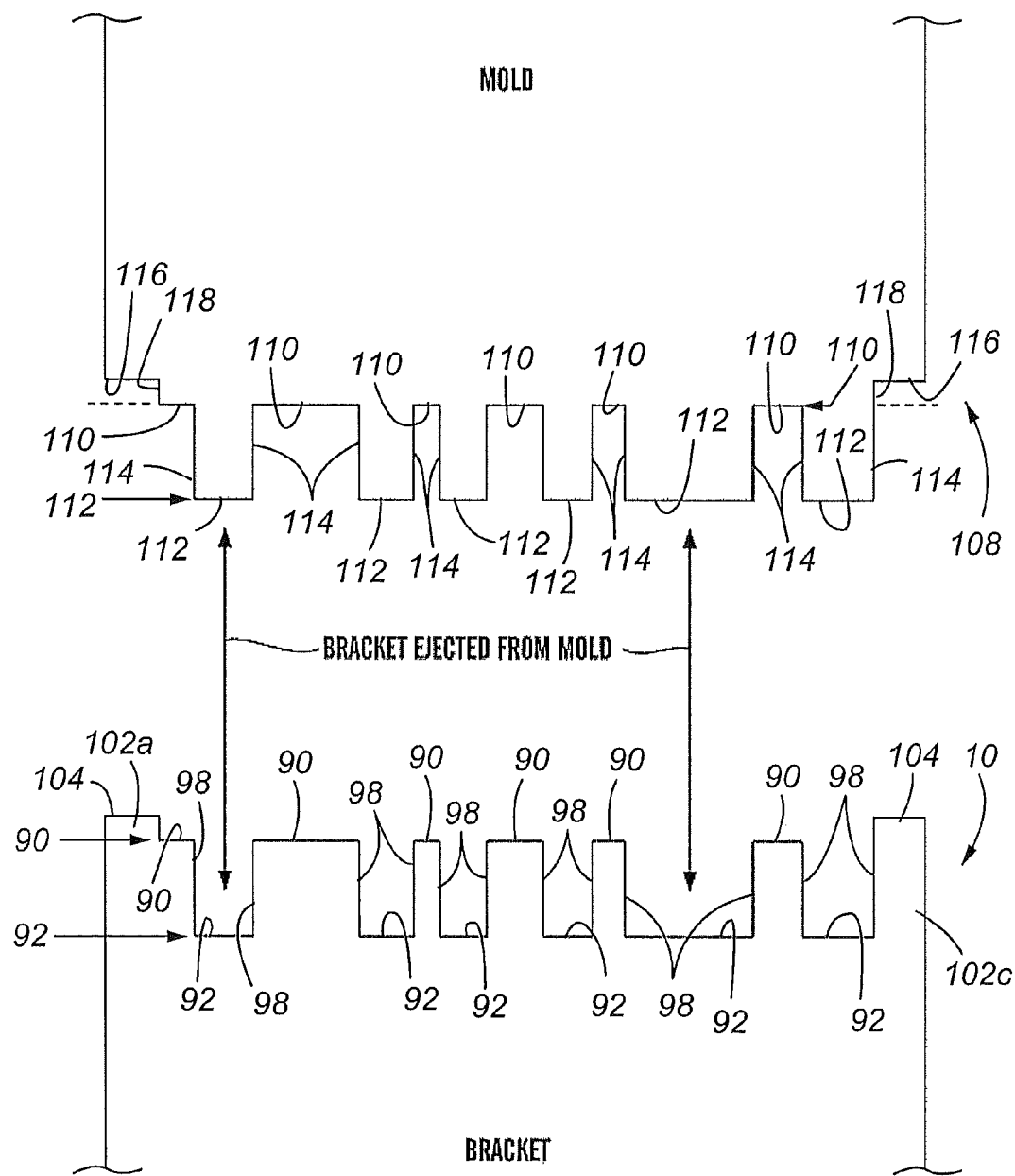
FIG. 17 is a cross-sectional view of a bracket and a mold used to form the bracket.

Referring now to FIG. 17, the mold 108 has a base that includes mold recessed surface 110 and mold projected surface 112, which correspond to the projected surface 90 and the recessed surface 92 of bracket 10, respectively. Preferably, mold recessed surface 110 and mold projected surface 112 have a surface finish of approximately a maximum of 110.8 micro-inches. In contrast, preferably the mold character walls 114 of mold 108 that form the generally sloped or perpendicular surfaces between characters 94 and intermediate spaces 96 of bracket 10 are polished. More specifically, the mold character walls 114 of mold 108 are preferably hand polished to a relatively smooth and polished finish, preferably using a ruby stone, although other means may be employed. Upon manufacture of a bracket 10 from mold 108, the hand polished character walls 114 of the mold 108 allow the actual bracket 10 to be ejected from the mold 108 because the character walls 98 of bracket 10 are formed to have a smooth and polished finish that corresponds to the polished mold character walls 114 from which they were formed. Thus, the bracket 10 may be ejected from mold 108 without sticking to the mold 108 and thereby preventing ejection from occurring, or bending or otherwise causing detrimental structural damage to the bracket 10 during the ejection process. An ejector pin (not shown) may be used to aid the ejection process, wherein the ejection pin forceably separates the bracket 10 from the mold 108 by pushing base 16 away from mold 108.

Where a perimeter rail is used, the mold 108 preferably includes a deeper recessed surface 116 corresponding to the perimeter rail surface 104. The deeper recessed surface 116 is surficially textured to provide texturing to the perimeter rail surface, which in turn improves bonding between the bracket 10 and the surface of the tooth. More particularly, the deeper recessed surface 116 of the mold 108 preferably has a surface finish of approximately a maximum of 110.8 micro-inches. In contrast, preferably the mold perimeter rail walls 118 of mold 108 are polished to a smooth finish to prevent an injected bracket 10 from sticking to the mold 108 during the ejection process, thereby preventing ejection or otherwise causing detrimental structural damage to the bracket 10 during the ejection process.

Figure 18:
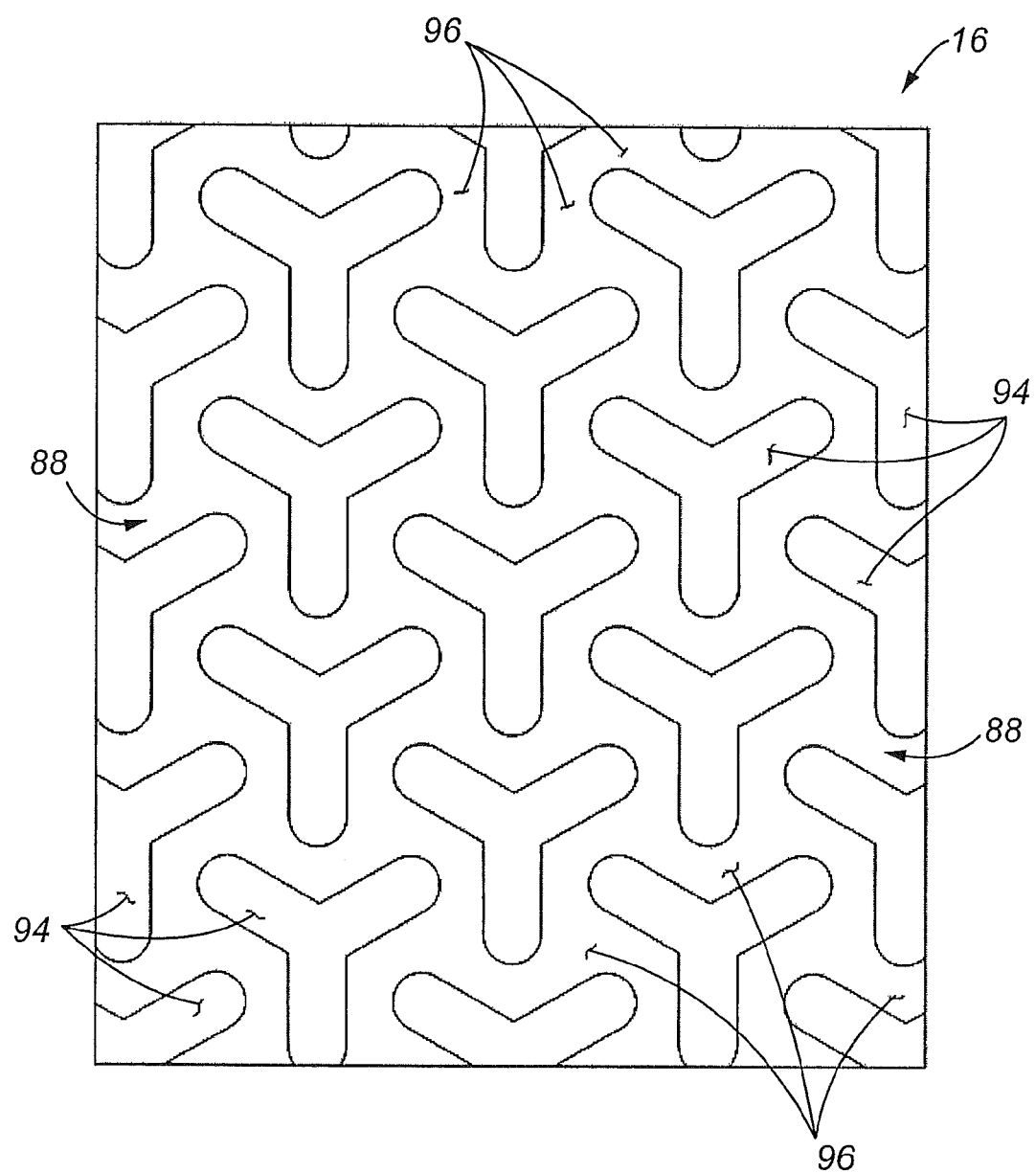
FIG. 18 is a separate embodiment of the present invention comprising an alternate base pattern.

Referring now to FIG. 18, an alternate aspect of the invention is shown. FIG. 18 presents a pattern of characters 94, wherein the characters are a three-pronged shape resembling the letter "Y". As in the previously described embodiments, intermediate space 96 surrounds the characters 94 within the interior region 88 of the base 16. Accordingly, the present invention contemplates the use of patterns of characters 94 wherein the character is a seemingly arbitrary shape, and one in which the base 16 possesses a projected surface 90 and a recessed surface 92. Brackets 10 that included patterns of characters 94 of shapes may further include discontinuous perimeter rail structures as described above.

Figure 19:
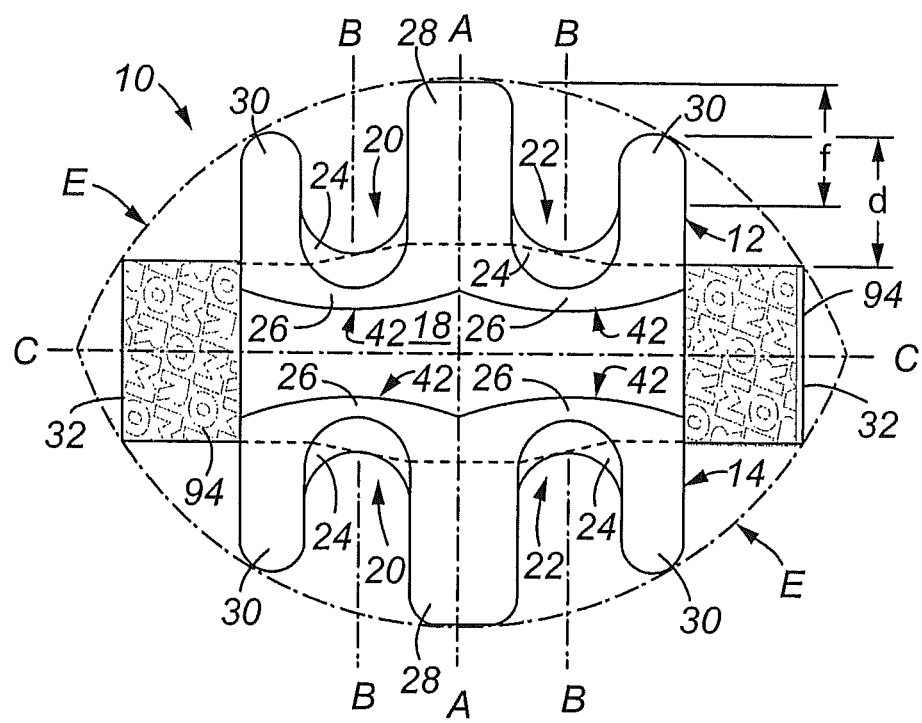
FIG. 19 is a labial view of a bracket having a labial positioned character pattern on its flange portions.

Referring now to FIG. 19, in a separate aspect of the invention, a pattern of characters 94 can be integrated into a side or labial position on the bracket 10. For example, as shown in FIG. 19, the flanges 32 can include a pattern of characters 94 such that the characters 94 are visible from a front view of the bracket 10. The pattern 94 could be a trademark of a manufacturer, a message, and/or the pattern 94 may be an ornamental or fanciful design.

In summary, the present invention is unique in that it provides a device for providing a continuous pattern of characters on the base of an orthodontic bracket. Characters are preferably formed by creating a recessed pattern of characters in the base, with the area between the characters raised, such that the area between the characters is closer to the tooth surface when the bracket is applied to the surface of a patient's tooth using an adhesive. Alternatively, the characters may be raised and projecting relative to the area between the characters, such that the characters are closer to the tooth surface when the bracket is attached to the surface of a patient's tooth.

In a separate aspect of the invention, a discontinuous perimeter rail may be used around the character pattern of the base. Preferably, the discontinuous perimeter rail includes four separate corner sections and two additional separate straight sections along the gingival and occlusal edges of the base. When used, the discontinuous perimeter rail projects beyond the patterned surface of the base, such that the discontinuous perimeter rail is closest to the tooth surface when the bracket is attached to a patient's tooth. The discontinuous perimeter rail increases the bonding strength of the bracket to the tooth's surface.

The substantially continuous pattern of characters and intermediate space formed on the base of an orthodontic bracket provides a texturing pattern (e.g., an ordered array of projecting features) for bonding the bracket to a patient's tooth using an adhesive, while at the same time providing a means of presenting information about the bracket on its base surface by advantageously utilizing characters that represent pertinent information, such as the name of the bracket manufacturer, the intended location for the bracket placement, or a graphics symbol or logo.

The invention presented herein has been described with respect to preferred embodiments; however, other changes and modifications to the invention may be made which are still contemplated within the spirit and scope of the invention.

The foregoing description of the present invention has been provided for purposes of illustration and description. This description is not intended to limit the invention and various modalities thereof. Variations, embodiments and modifications will be apparent to those skilled in the art and are intended to be within the scope of the following claims.

What is claimed is:

1. An orthodontic bracket comprising: a body having an archwire slot to accommodate an archwire between two opposing tie wings, said archwire slot having at least one of a convex sidewall and a floor portion adapted to reduce archwire bracket frictional engagement, and an auxiliary slot extending in a gingival/occlusal direction under said floor portion, said auxiliary slot configured to receive one of a steel ligature or an auxiliary shaft, said auxiliary slot being open at either end thereof, and having complementary flat outer sidewalls and a surface including two or more characters selected from the group consisting of letters and numbers that are spaced apart from each other, said two or more characters being projected from said surface and having spaces between said two or more characters being recessed, said body made solely of a material selected from the group consisting of plastic, metal, and ceramic, wherein said two or more characters convey to a user of said bracket information selected from the group consisting of: model number, manufacturer, date of manufacture, lot number, distributor, placement data, and bracket data.

2. The bracket as claimed in claim 1, wherein between said two or more characters is an intermediate space, wherein said characters and said intermediate space are separated by a character wall.

3. The bracket as claimed in claim 1, wherein the two or more characters include a continuous series of alpha-numeric characters that form a pattern.

4. The bracket as claimed in claim 1, wherein the two of more characters is one of a trademark, a message, an ornamental design and a fanciful design.

5. An orthodontic bracket comprising: a body made solely of a material selected from the group consisting of plastic, metal, and ceramic having an archwire slot to accommodate an archwire between two opposing tie wings, an auxiliary slot passing under the archwire slot, said auxiliary slot configured to receive one of a steel ligature or an auxiliary shaft, when the bracket is bonded to a subject's teeth, said auxiliary slot, having a surface including two or more characters selected from the group consisting of letters and numbers that are spaced apart from each other, said two or more characters being recessed from said surface and having spaces between said two or more characters being projected, wherein said two or more characters convey to a user of said bracket information selected from the group consisting of: model number, manufacturer, date of manufacture, lot number, distributor, placement data, trademark, name, symbol, logo, part number and bracket data.

6. The bracket as claimed in claim 5, wherein said archwire slot extends gingivally and the auxiliary slot is positioned under said archwire slot to conserve a height of the bracket and enhance patient comfort.

7. The bracket as claimed in claim 6, wherein the two or more characters are integrated into the auxiliary slot and said characters have different dimensions.

8. The bracket as claimed in claim 5, wherein said two or more characters serves as texturing on the surface.

9. The bracket as claimed in claim 5, wherein the two or more characters are alpha numeric.

10. The bracket as claimed in claim 5, wherein the auxiliary slot has an inner-configuration that restricts rotation of complementary auxiliaries inserted in the auxiliary slot.

11. The bracket as claimed in claim 5, wherein said auxiliary slot extends gingivally/occlusually.

12. The bracket as claimed in claim 5, further comprising a second auxiliary slot, wherein each one of the auxiliary slot and the second auxiliary slot is on each side of a gingival-occlusal center plane of the bracket.

13. The bracket as claimed in claim 5, wherein said auxiliary slot has square corners.

14. The bracket as claimed in claim 5, wherein each of said two or more characters have a width of between about 0.034 and 0.038 inches and a line width of from between 0.008 and 0.010 inches.

15. The bracket as claimed in claim 5, wherein the two or more characters in the auxiliary slot have a rounded exterior surface.

16. The bracket as claimed in claim 5, wherein said bracket has a flange and said flange includes a continuous pattern of characters.

17. The bracket as claimed in claim 5, wherein the bracket has two flanges that include a pattern of characters.

18. An orthodontic bracket comprising: a body made solely of a material selected from the group consisting of plastic, metal, and ceramic having an archwire slot to accommodate an archwire, said archwire slot having at least one of a convex sidewall and a convex floor portion adapted to reduce archwire bracket frictional engagement, and at least one auxiliary slot that passes under the floor portion, said auxiliary slot configured to receive one of a steel ligature or an auxiliary shaft, said auxiliary slot being open at either end thereof, and having a surface including two or more characters selected from the group consisting of letters and numbers that are spaced apart from each other, said two or more characters being recessed from said surface and having spaces between said two or more characters being projected, wherein said two or more characters are molded and depict a trademark, name, symbol, logo, or part number, wherein each character has a width of between about 0.034 and 0.038 inches and wherein a line width of each character is from between 0.008 and 0.010 inches.

19. The bracket as claimed in claim 18, wherein the two or more characters form a pattern and the pattern is one of a trademark, a message, an ornamental design and a fanciful design.

20. The bracket as claimed in claim 18, wherein said auxiliary slot extends gingivally/occlusually.

21. The bracket as claimed in claim 18, wherein said bracket has a flange and said flange includes a continuous pattern of the two or more characters.

* * * * *